US011090025B2

(12) United States Patent
Mukdadi et al.

(10) Patent No.: US 11,090,025 B2
(45) Date of Patent: Aug. 17, 2021

(54) SYSTEM AND DEVICE FOR TUMOR CHARACTERIZATION USING NONLINEAR ELASTOGRAPHY IMAGING

(71) Applicants: Osama M. Mukdadi, Morgantown, WV (US); Ahmed M. Abdulhameed Sayed, Morgantown, WV (US); Ginger P. Layne, Morgantown, WV (US); Jame Abraham, Solon, OH (US)

(72) Inventors: Osama M. Mukdadi, Morgantown, WV (US); Ahmed M. Abdulhameed Sayed, Morgantown, WV (US); Ginger P. Layne, Morgantown, WV (US); Jame Abraham, Solon, OH (US)

(73) Assignee: West Virginia University, Morgantown, WV (US)

( * ) Notice: Subject to any disclaimer, the term of this patent is extended or adjusted under 35 U.S.C. 154(b) by 219 days.

(21) Appl. No.: 14/201,034

(22) Filed: Mar. 7, 2014

(65) Prior Publication Data
US 2014/0288424 A1 Sep. 25, 2014

Related U.S. Application Data

(60) Provisional application No. 61/775,555, filed on Mar. 9, 2013.

(51) Int. Cl.
*A61B 8/00* (2006.01)
*A61B 8/08* (2006.01)

(52) U.S. Cl.
CPC ............. *A61B 8/403* (2013.01); *A61B 8/085* (2013.01); *A61B 8/4483* (2013.01); *A61B 8/483* (2013.01);

(Continued)

(58) Field of Classification Search
CPC ....... A61B 8/403; A61B 8/4483; A61B 8/085; A61B 8/5223; A61B 8/483; A61B 8/485; A61B 8/4494; A61B 8/5207
See application file for complete search history.

(56) References Cited

U.S. PATENT DOCUMENTS 5,524,636 A * 6/1996 Sarvazyan et al. ............ 600/587
7,901,357 B2 * 3/2011 Boctor ..................... A61B 8/08
600/437

(Continued)

OTHER PUBLICATIONS

Wang ZG, Liu Y, Wang G, Sun LZ. Elastography Method for Reconstruction of Nonlinear Breast Tissue Properties. International Journal of Biomedical Imaging. 2009;2009:406854. doi:10.1155/2009/406854.*

(Continued)

*Primary Examiner* — Hien N Nguyen
(74) *Attorney, Agent, or Firm* — Buchanan Ingersoll & Rooney PC; Craig G. Cochenour, Esq.

(57) ABSTRACT

The present invention provides a method and a device to image and characterize human tumors, and to classify the tumors as either malignant or benign. The method includes using a multi-compression technique upon the tissue or organ combined with a 3D ultrasound strain imaging of the compressed tissue or organ for acquiring raw data and analyzing the raw data using a computer processing unit equipped with a nonlinear biomechanical tissue model for tumor classification. A device is provided having a compression stage for delivering multi-compression with continuous force measurements, and a 3D ultrasound transducer strain imaging probe, wherein the imaging probe and the compression stage are in communication with a computer processing unit.

17 Claims, 21 Drawing Sheets a)

b)

(52) U.S. Cl.
CPC .......... *A61B 8/485* (2013.01); *A61B 8/5223* (2013.01); *A61B 8/4494* (2013.01); *A61B 8/5207* (2013.01)

(56) References Cited

U.S. PATENT DOCUMENTS

| | | | | |
|---|---|---|---|---|
| 2005/0119568 | A1* | 6/2005 | Salcudean | A61B 8/08 600/437 |
| 2005/0283076 | A1* | 12/2005 | Hangiandreou | A61B 8/0825 600/443 |
| 2009/0198129 | A1* | 8/2009 | Varghese | A61B 8/0858 600/438 |
| 2013/0296707 | A1* | 11/2013 | Anthony | A61B 8/13 600/459 |
| 2014/0094702 | A1* | 4/2014 | Kim | G01N 29/0654 600/438 |
| 2014/0180058 | A1* | 6/2014 | Khan | G01R 33/56358 600/410 |

OTHER PUBLICATIONS

Hall, Timothy J., et al. "Elastic nonlinearity imaging." Engineering in Medicine and Biology Society, 2009. EMBC 2009. Annual International Conference of the IEEE. IEEE, 2009.*

Kobayashi, Yo, et al. "Development and validation of a viscoelastic and nonlinear liver model for needle insertion." International journal of computer assisted radiology and surgery 4.1 (2009): 53-63.*

Kobayashi, Palpation Nonlinear Reaction Force Analysis for Characterization of Breast Tissues, 33rd Annual International Conference of the IEEE EMBS Boston, Massachusetts USA, Aug. 30-Sep. 3, 2011 (Year: 2011).*

Kobayashi, Yo, et al. "Development and validation of a viscoelastic and nonlinear liver model for needle insertion." International journal of computer assisted radiology and surgery 4.1 (2009): 53-63. (Year: 2009).*

Chang, 3-D ultrasound strain images for breast cancer diagnosis, International Congress Series 1281 (2005) 1069-1074 (Year: 2005).*

Moon, Analysis of Elastographic and B-mode features at sonoelastography for breast tumor classification, Ultrasound in Med. & Biol., vol. 35, No. 11, pp. 1794-1802, 2009 (Year: 2009).*

Shanmugam, Simulation of Breast Tissue: A Study to Evaluate Optimal Compression Dynamics, 2005 Asian Conference on Sensors and the International Conference on New Techniques in Pharmaceutical and Biomedical Research, 148-150 (Year: 2005).*

Thitaikumar, A. et al., Breast Tumor Classification Using Axial Shear Strain Elastography: A Feasibility Study, Phys. Med. Biol., 2008, 4809-4823, vol. 53, IOP Publishing.

Konofagou, E.E., Shear Strain Estimation and Lesion Mobility Assessment in Elastography, Ultrasonics, 2000, 400-404, vol. 38, Elsevier.

Improved Detection of Abnormalities with Elastography, 2004 Koninklijke Philips Electronics N.V., http://www.healthcare.philips.com/us_en/products/ultrasound/technologies/elastography.wpd.

Tan, S.M., Improving B Mode Ultrasound Evaluation of Breast Lesions With Real-Time Ultrasound Elastography—A Clinical Approach, The Breast—www.ScienceDirect, 2008, 252-257, vol. 17, ScienceDirect, Elsevier.

* cited by examiner a.)

b.)

Table 1. Inclusion volume estimations for the breast phantom.

|  | Volume (mm$^3$) | Error | Radius (mm) |
|---|---|---|---|
| Actual size | 381.704 |  | 4.50 |
| Axial Strain | 352.076 | -7.76% | 4.38 |
| First Principal | 367.297 | -3.77% | 4.44 |
| Maximum Shear | 382.807 | 0.29% | 4.50 |
| Von Mises | 394.821 | 3.44% | 4.55 |

FIG. 15

Table 2  Elastographic tumor classification methods comparison.

| Classification Method | Advantages | Disadvantages |
|---|---|---|
| Proposed Method (Tissue nonlinearity) | • Accurate mass differentiation.<br>• Addresses tissue mechanics and nonlinearity.<br>• Can be extended to classify other organ's tumors. | • Requires multi-compression.<br>• Requires force monitoring.<br>• Requires operator training. |
| Relative volume | • Good mass differentiation. | • Requires extensive operator training.<br>• Some malignant masses are not well bounded on B-mode images, lead to inaccurate results.<br>• Limited for breast masses. |
| Relative stiffness | • Can be used to classify other organ's tumors. | • Requires operator training.<br>• Parameter overlaps between mass types. |

FIG. 21

SYSTEM AND DEVICE FOR TUMOR CHARACTERIZATION USING NONLINEAR ELASTOGRAPHY IMAGING

CROSS-REFERENCE TO RELATED APPLICATION

This utility patent application claims the benefit of priority to U.S. Provisional Patent Application Ser. No. 61/775,555, filed on Mar. 9, 2013. The entire contents of U.S. Provisional patent Application Ser. No. 61/775,555 is incorporated by reference into this utility patent application as if fully written herein.

STATEMENT REGARDING FEDERALLY SPONSORED RESEARCH OR DEVELOPMENT

This invention was made with government support under contract number 5R21DE019561 by the National Institute of Health (NIH). The government has certain rights in the invention.

BACKGROUND OF THE INVENTION

1. Field of the Invention

The present invention provides method for non-invasive classification of human tumors using ultrasound elastography via constructing quantitative tissue strain images and volumes. A device is provided comprising a 3D ultrasound transducer and a compression stage or paddle, each of which are in communication with a computer processing unit. The device's functions are applying controlled and precise tissue compression and acquiring ultrasound radio frequency data regarding an examined tissue.

2. Description of the Background Art

Current state of research in the field of tumor classification is set forth below:

1. X-ray imaging: This method uses ionizing radiation, which is unfavorable with pregnant patients. For breast masses, mammography is the current clinical imaging modality for breast masses. It has high sensitivity for detecting tumors, yet for patients with dense tissues, the sensitivity declines.
2. Conventional ultrasound imaging: this imaging method has the disadvantage of the low sensitivity and specificity rates when used alone.
3. Magnetic resonance imaging: has a good sensitivity rates for detecting malignancy. It has the disadvantages of lower specificity rates, being cost inefficient and not suitable with patients having metal implants.
4. Computed tomography: This method uses ionizing radiation, which is unfavorable with pregnant patients. It has good contrast with the ability to show tumor margins. However this method suffers from technological issues that need solving before applying it clinically.
5. The routine use of biopsy procedures to obtain tissue samples and histologically diagnose tumors. This method has the disadvantage of being invasive.
6. The use of strain imaging in the classification of tumors based on a linear elastic tissue model. These methods have the disadvantage of an existing overlap between the classification parameters used.
7. The use of shear wave elastography to visualize tumors and classify based on the estimated elasticity parameters. It has the disadvantage of not being able to diagnose very hard tumors.

Background publications and patents are as follows:
1. J. Ophir, I. Cespedes, H. Ponnekanti, Y. Yazdi, X. Li, Elastography—A Quantitative Method For Imaging The Elasticity Of Biological Tissues, Ultrasonic Imaging, 13 (1991) 111-134.
2. T. A. Krouskop, T. M. Wheeler, F. Kallel, B. S. Garra, T. Hall, Elastic Moduli Of Breast And Prostate Tissues Under Compression, Ultrasonic Imaging, 20 (1998) 260-274.
3. E. S. Burnside, T J. Hall, A. M. Sommer, O. K. Hesley, G. A. Sisney, W. E. Svensson, J. P. Fine, J J. Jiang, N. J. Hangiandreou, Differentiating Benign From Malignant Solid Breast Masses With US Strain Imaging. Radiology, 245 (2007) 401-410.
4. G. Scaperrotta, C. Ferranti, C. Costa, L. Mariani, M. Marchesini, L. Suman, C. Folini, S. Bergonzi, Role Of Sonoelastography In Non-Palpable Breast Lesions, European Radiology, 18 (2008) 2381-2389.
5. Y. P. Qiu, M. Sridhar, J. K. Tsou, K. K. Lindfors, M. F. Insana, Ultrasonic Viscoelasticity Imaging Of Nonpalpable Breast Tumors: Preliminary Results, Acad Radiol, 15 (2008) 1526-1533.
6. S. Bharat, T. G. Fisher, T. Varghese, T. J. Hall, J. Jiang, E. L. Madsen, J. A. Zagzebski, F. T. Lee, Three-Dimensional Electrode Displacement Elastography Using The Siemens C7F2 Foursight Four-Dimensional Ultrasound Transducer, Ultrasound Med Biol, 34 (2008) 1307-1316.
7. N. Houssami, S. J. Lord, S. Ciatto, Breast Cancer Screening: Emerging Role Of New Imaging Techniques As Adjuncts To Mammography, Medical Journal of Australia, 190 (2009) 493-498.
8. S. P. Poplack, P A. Carney, J. E. Weiss, L. Titus-Erastoff, M. E. Goodrich, A. N. A. Tosteson, Screening Mammography: Costs And Use Of Screening-Related Services, Radiology, 234 (2005) 79-85.
9. H. Zhi, X. Y. Xiao, H. Y. Yang, B. Ou, Y. L. Wen, B. M. Luo, Ultrasonic Elastography in Breast Cancer Diagnosis: Strain Ratio vs 5-pomt Scale, Acad Radiol, 17 (2010) 1227-1233.
10. A. A. Oberai, N. H. Gokhale, S. Goenezen, P. E. Barbone, T. J. Hall, A. M. Sommer, J. F. Jiang, Linear And Nonlinear Elasticity Imaging Of Soft Tissue In vivo: Demonstration Of Feasibility, Phys Med Biol, 54 (2009) 1191-1207.
11. J. Ophir, S. Srinivasan, R. Righetti, A. Thittai, Elastography: A Decade Of Progress (2000-2010), Curr Med Imaging Rev, 7 (2011) 292-312.
12. F. K. W. Schaefer, I. Heer, P. J. Schaefer, C. Mundhenke, S. Osterholz, B. M. Order, N. Hofheinz, J. Hedderich, M. Heller, W. Jonat, I. Schreer, Breast Ultrasound Elastography-Results Of 193 Breast Lesions In A Prospective Study With Histopathologic Correlation, Eur J Radiol, 77 (2011) 450-456.
13. R. G. Barr, Sonographic Breast Elastography, J Ultras Med, 31 (2012) 773783.
14. J. P. Xu, S. Tripathy, J. M. Rubin, R. W. Stidham, L. A. Johnson, P. D. R. Higgins, K. Kim, A New Nonlinear Parameter In The Developed Strain-To-Applied Strain Of The Soft Tissues And Its Application In Ultrasound Elasticity Imaging. Ultrasound Med Biol, 38 (2012) 511-523.

SUMMARY OF THE INVENTION

One embodiment of the present invention provides a method for classifying and characterizing a tumor of a patient as either benign or malignant comprising positioning a tissue or organ of a patient on a compression stage, aligning a 3D (three dimensional) ultrasound probe on or in the vicinity of the tissue or organ suspected of having a tumor, the probe capable of performing 3D ultrasound strain imaging (elastography), applying a first compression force to the tissue or organ having the suspected tumor for forming a first compressed tissue or organ, performing 3D ultrasound strain imaging (elastography) to the first compressed tissue or organ for estimating tissue strain, applying a second compression force to the first compressed tissue or organ, wherein the second compression force is greater than the first compressive force for forming a second compressed tissue or organ, performing 3D ultrasound strain imaging (elastography) to the second compressed tissue or organ for estimating tissue strain, optionally applying three or more successive compression forces to the second compressed tissue or organ having the suspected tumor, and performing 3D ultrasound strain imaging (elastography) to the second compressed tissue or organ for estimating tissue strain, constructing strain images and volumes, and performing a tissue characterization and classification procedure using an estimated nonlinear parameter model and determining whether the tissue or organ has a benign tumor or a malignant tumor. In a preferred embodiment of this method, the method includes wherein the first, the second and a third compression force is applied against the tissue or organ. The compression force is in the form of pressure applied to the tissue or organ by mechanical means, such as a compression stage or plate.

In another embodiment of this method as described herein, the method includes wherein the 3D ultrasound strain imaging probe acquires volumetric raw data and transfers said volumetric raw data to a computer processing unit for constructing strain elastography volumes at each pre-compression level, calculating the strain difference values between the suspected tumor (stiff tumor) and a background soft tissue(s), plotting the strain difference values for all pre-compression levels together for forming a plot, observing from the plot the rate of change of strain difference values, and classifying the tumor as benign if the degree of increase of strain difference values with the pre-compression levels is very slow or nearly zero indicating weak nonlinear behavior for the suspected tumor, or classifying the suspected tumor as malignant if the degree of increase was high indicating high nonlinear behavior.

Another embodiment of this invention provides a device comprising a 3D (three dimensional) ultrasonic transducer (probe) that acquires raw image and volumetric data when positioned against and scanning a tissue or organ of a patient, a processing unit in communication with the 3D ultrasound transducer for analyzing the raw data transferred from the 3D ultrasonic transducer to the computer processing unit, the computer processing unit constructs a final set of images and volumes from multiple compression and ultrasound raw data, and performs the classification of the tissue or organ using a nonlinear biomechanical analysis.

In yet another embodiment of this invention, the device, as described herein, includes a compression stage for applying pressure against the tissue or organ of a patient. Preferably, the compression stage applies continuous force measurements to the tissue or organ.

Yet another embodiment of the device of the present invention, as described herein, includes wherein the 3D ultrasound transducer uses an ultrasound linear array.

Another embodiment of the device of the present invention, as described herein, includes wherein the 3D ultrasound transducer is a linear probe that is either a mechanically swept 1-D array, or a 2-D array of transducers.

Another embodiment of the device of the present invention, as described herein, includes wherein the compression stage is a motorized standalone compression stage for obtaining fast and accurate compression force measurements, the motorized compression stage having the ability to freely maneuver around the suspected tissue or organ, the motorized compression stage controlled by a computer processor. In a preferred embodiment of this invention, the device includes wherein the motorized compression stage holds the 3D ultrasound transducer for maneuvering the 3D ultrasound transducer about the suspected tissue or organ having a tumor. Preferably, the motorized compression stage has an aperture (for example, a hole, an opening, a slot, or a slit) for allowing the 3D ultrasound transducer to scan a localized area of interest of a tissue or organ. In a most preferred embodiment, the motorized compression stage applies precise multiple-compression levels to the tissue or organ, controlled by the computer processing unit.

In another embodiment of this invention, the device, as described herein, includes wherein the 3D ultrasound transducer comprises either a mechanically actuated array of piezoelectric elements, or a two dimensional array of elements, wherein the 3D transducer acquires raw radiofrequency (RF) signals when applied against a tissue or organ of a patient.

Another embodiment of this invention provides a device, as described herein, including a force gauge that is attached to and in communication with the 3D ultrasound transducer probe for providing continuous force measurements, which enables a smooth force-strain measurement.

BRIEF DESCRIPTION OF THE DRAWINGS

FIG. 21 Sets forth a table comparison of elastographic tumor classification methods and their respective advantages and disadvantages.

DETAILED DESCRIPTION OF THE INVENTION

Figure 1:
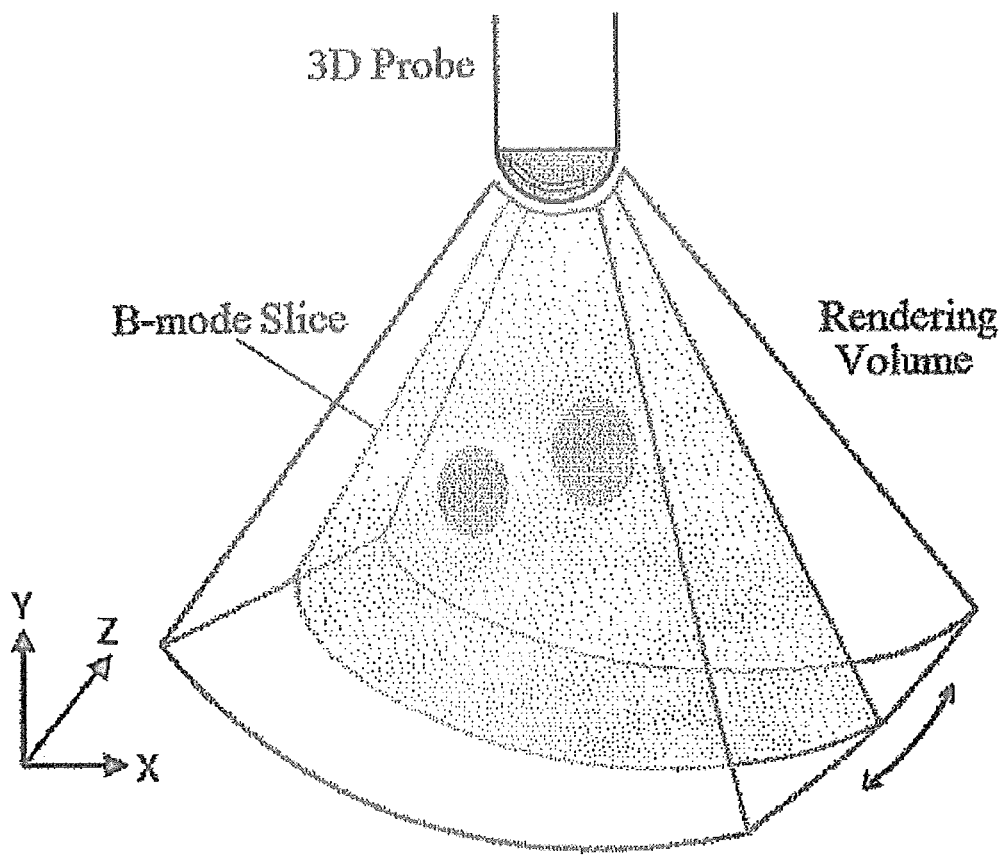
FIG. 1 Shows a 3D ultrasound probe sweeping motion.

The present invention provides a method for classifying and characterizing a tumor of a patient as either benign or malignant comprising positioning a tissue or organ of a patient on a compression stage, aligning a 3D (three dimensional) ultrasound probe on or in the vicinity of the tissue or organ suspected of having a tumor, the probe capable of performing 3D ultrasound strain imaging (elastography), applying a first compression force to the tissue or organ having the suspected tumor for forming a first compressed tissue or organ, performing 3D ultrasound strain imaging (elastography) to the first compressed tissue or organ for estimating tissue strain, applying a second compression force to the first compressed tissue or organ, wherein the second compression force is greater than the first compressive force for forming a second compressed tissue or organ, performing 3D ultrasound strain imaging (elastography) to the second compressed tissue or organ for estimating tissue strain, optionally applying three or more successive compression forces to the second compressed tissue or organ having the suspected tumor, and performing 3D ultrasound strain imaging (elastography) to the second compressed tissue or organ for estimating tissue strain, constructing strain images and volumes, and performing a tissue characterization and classification procedure using an estimated nonlinear parameter model and determining whether the tissue or organ has a benign tumor or a malignant tumor. In a preferred embodiment of this method, the method includes wherein the first, the second and a third compression force is applied against the tissue or organ. The compression force is in the form of pressure applied to the tissue or organ by mechanical means, such as a compression stage or plate.

In another embodiment of this method as described herein, the method includes wherein the 3D ultrasound strain imaging probe acquires volumetric raw data and transfers said volumetric raw data to a computer processing unit for constructing strain elastography volumes at each pre-compression level, calculating the strain difference values between the suspected tumor (stiff tumor) and a background soft tissue(s), plotting the strain difference values for all pre-compression levels together for forming a plot, observing from the plot the rate of change of strain difference values, and classifying the tumor as benign if the degree of increase of strain difference values with the pre-compression levels is very slow or nearly zero indicating weak nonlinear behavior for the suspected tumor, or classifying the suspected tumor as malignant if the degree of increase was high indicating high nonlinear behavior.

Another embodiment of this invention provides a device comprising a 3D (three dimensional) ultrasonic transducer (probe) that acquires raw image and volumetric data when positioned against and scanning a tissue or organ of a patient, a processing unit in communication with the 3D ultrasound transducer for analyzing the raw data transferred from the 3D ultrasonic transducer to the computer processing unit, the computer processing unit constructs a final set of images and volumes from multiple compression and ultrasound raw data, and performs the classification of the tissue or organ using a nonlinear biomechanical analysis.

In yet another embodiment of this invention, the device, as described herein, includes a compression stage for applying pressure against the tissue or organ of a patient. Preferably, the compression stage applies continuous force measurements to the tissue or organ.

Yet another embodiment of the device of the present invention, as described herein, includes wherein the 3D ultrasound transducer uses an ultrasound linear array.

Another embodiment of the device of the present invention, as described herein, includes wherein the 3D ultrasound transducer is a linear probe that is either a mechanically swept 1-D array, or a 2-D array of transducers.

Another embodiment of the device of the present invention, as described herein, includes wherein the compression stage is a motorized standalone compression stage for obtaining fast and accurate compression force measurements, the motorized compression stage having the ability to freely maneuver around the suspected tissue or organ, said motorized compression stage controlled by a computer processor. In a preferred embodiment of this invention, the device includes wherein the motorized compression stage holds the 3D ultrasound transducer for maneuvering the 3D ultrasound transducer about the suspected tissue or organ having a tumor. The motorized compression stage applies precise compression levels to the tissue or organ.

In another embodiment of this invention, the device, as described herein, includes wherein the 3D ultrasound transducer comprises either a mechanically actuated array of piezoelectric elements, or a two dimensional array of elements, wherein the 3D transducer acquires raw radiofrequency (RF) signals when applied against a tissue or organ of a patient.

Another embodiment of this invention provides a device, as described herein, including a force gauge that is attached to and in communication with the 3D ultrasound transducer probe for providing continuous force measurements, which enables a smooth force-strain measurement.

The present invention has several uses:
1. It can be used by radiologists and technicians to classify and characterize human tumors at the very early stage.
2. The method can help limit the number of unnecessary benign biopsy procedures, for example benign breast masses.
3. It can be used to predict the actual mass morphology and also estimate its size.

The present invention solves an existing problem which is noninvasive and safe classification of human tumors. Background art methods suffer from unclear distinction between malignant and benign tumors. The currently trusted clinical method, biopsy, is invasive and delivers unnecessary pain to the benign cases.

The present invention includes a 3D ultrasonic transducer that can be placed on the examined tissue for imaging as well as for tissue compression. The operator determines the region of interest (ROI) and compression levels. The acquired volumetric raw data is transferred from the scanning system to a processing unit that constructs the final images and volumes, and also performs the classification analysis. A pilot successful study on breast masses was performed to evaluate the classification method of the present invention. The present method may be used to classify and detect other tissue types like prostate, liver and kidney tissues, as well.

The present invention has several improvements or advantages over existing methods such as:
1. The methods and system configuration and device of the present invention provides a better classification and distinction between mass types, than the current known methods based on ultrasound elastography.
2. The present method of this invention produces much less pain when compared with known clinical methods that use biopsy.

The present invention includes the use of a nonlinear biomechanical tissue model in the classification process, rather than a linear elastic model. The present invention utilizes a multi-compression technique in the data acquisition process with a safe and user friendly setup that has been tested on in vivo breast cases. The multi-compression is delivered through a compression stage (unit) with continuous force measurements. The present invention thus provides simplicity in the testing procedures.

The method of the present invention provides a method and a device to image and characterize human tumors, and classify them as either malignant or benign. The method of the present invention comprises the following steps:
1. Position the patient on the compression stage, and align the 3D ultrasound probe on the suspected tissue.
2. Apply multi-compression using with the 3D probe at different levels.
3. Apply an additional small compression at each level to estimate tissue strains.
4. Construct strain images and volumes.
5. Perform the tissue classification procedure using the estimated nonlinear parameter.

In this method, certain conditions are preferably avoided:
1. The low resolution force measurements obtained from the compression stage. This can be overcome with the use of a separate high resolution force gauge attached to the probe.
2. Our initial investigation was performed at three levels of pre-compression. More levels can be obtained by using the custom compression stage that performs the pre-compression automatically and acquire data.

The present method includes several variations that will be appreciated by those persons skilled in the art, such as for example, but not limited to the following:

1. The use of 3D ultrasound linear array instead of 3D sector one. The linear probe can be either a mechanically swept 1-D array, or a 2-D array of transducers.

2. Designing and implementing a motorized standalone compression stage to obtain fast and more accurate compression force measurements, with the ability to freely maneuver around the suspected tissue.

The device of this invention includes a custom compression stage to hold the 3D probe with maneuvering flexibility around the target tumor, and for applying precise compression levels, and for acquiring radio frequency data.

The method and the device of this invention fulfills the current unmet needs:

1. Cancer in general can travel to other healthy organs because of metastasis, unless an early detection was available.

2. Breast cancer is the most common cancer among women in the United States, after lung cancer. It caused about 13.7% of overall women deaths due to cancer.

3. The low sensitivity of the used imaging methods motivates the development of this IP.

4. The invasive nature of biopsy and the fact that about 76% of biopsies routinely performed yield benign results, which are considered unnecessary biopsies. This unnecessary painful procedure can be eliminated by using the proposed IP.

5. This IP produces less or no pain when comparing with biopsy procedures.

6. The use of shear wave elastography suffers from showing no results for very hard lesions, which limits the classification capabilities.

7. Currently used strain imaging methods show good classification performance, yet an overlap exits in the parameters used for classification.

8. The use of the classification imaging method in 3D provides more information and details about the suspected tumor's type (diagnosis) and also tumor's estimated volume.

9. Classification based on the new nonlinear parameter outperforms other commonly used methods for tumor classification.

This invention provides a new tumor classification method based on ultrasound strain imaging (elastography). The method is making use of a nonlinear biomechanical model. The method is primarily used for classifying stiff tumors as either benign or malignant (cancer). The device of the present invention comprises the following elements:

1. A 3D ultrasound transducer comprises either a mechanically actuated array of piezoelectric elements, or a two dimensional array of elements. The transducer is used to acquire raw radiofrequency (RF) signals for the examined tissue. Pre-compression pressure is applied using the 3D ultrasound probe on the investigated tissue at three different levels or more (a process called multi-compression). At each level an additional small compression is applied to estimate strains and produce strain images and volumes at that specific level. A standalone compression stage is employed to apply compression pressure automatically at multi levels via computer controlled motors. This stage can also provide probe maneuvering capabilities. A force gauge is attached to the probe for continuous force measurements, which enables a smooth force-strain measurement.

2. Using the constructed strain elastography volumes at each pre-compression level, the strain difference values between the suspected stiff tumor and the background soft tissues are calculated. All strain difference values for all pre-compression levels are plotted together and their rate of change is observed. A tumor is classified as benign if the degree of increase of strain difference values with the pre-compression levels is very slow or nearly zero. The small increase in strain difference values indicates weak nonlinear behavior for the suspected tumor, which suggests benignity. On the other hand, a tumor is classified as malignant one, if the degree of increase was high, indicating high nonlinear behavior.

3. A nonlinear parameter is used as a quantification measure for the degree of tumor nonlinearity, using an empirical power-law relationship between pre-compression force and strain differences. Curve fitting is applied on the estimated data using this power relationship to describe the strain differences degree of change with the multi-compression levels. The following equation describes the nonlinear power-law behavior:

$$f = A(\Delta\epsilon)^n$$

where f is the applied force level, As is the strain difference between the suspected tumor and surrounding healthy soft tissues. The A and n are generalized fitting parameters, where n is considered the main nonlinear parameter characterizing the tumor type. This nonlinear parameter provided a clear classification region between malignant and benign tumors. Initial studies show that the nonlinear parameter values for malignant tumors are greater than 1.5, while benign tumors had values of much less than 0.5.

Those persons skilled in the art will understand that the present invention provides a new nonlinear elastography based classification method for examining masses that may occur in a patients anatomy, such as for example but not limited to, human breast masses. Multi-compression elastography imaging is elucidated in this study to differentiate malignant from benign lesions, based on their nonlinear mechanical behavior under compression. Three classification parameters were used and compared in this work: a new nonlinear parameter based on a power-law behavior of the strain difference between breast masses and healthy tissues, mass-soft tissue strain ratio and the mass relative volume between B-mode and elastography imaging. Using 3D elastography, these parameters were tested in vivo. A pilot study on ten patients was performed, and results were compared with biopsy diagnosis as a gold standard. Initial elastography results showed a good agreement with biopsy outcomes. The new estimated nonlinear parameter had an average value of 0.163±0.063 and 1.642±0.261 for benign and malignant masses, respectively. Strain ratio values for the benign and malignant masses had an average value of 2.135±0.707 and 4.21±2.108, respectively. Relative mass volume was 0.848±0.237 and 2.18±0.522 for benign and malignant masses. In addition to the traditional normal axial strain, new strain types were used for elastography and constructed in 3D, including the first principal, maximum shear and Von Mises strains. The new strains provided an enhanced distinction of the stiff lesion from the soft tissue. In summary, the proposed elastographic techniques can be used as a noninvasive quantitative characterization tool for breast cancer, with the capability of visualizing and separating the masses in a three dimensional space. This may reduce the number of unnecessary painful breast biopsies.

Worldwide, breast cancer comprises about 22.9% of all types of cancer in women. This type of cancer caused 458,503 deaths worldwide, which is equivalent to 13.7% of female deaths due to cancer (see reference 1). According to a recent report in the United States, breast cancer is considered the second leading cause of death among women due to cancer, after lung cancer (see reference 2). The sensitivity of mammography for breast cancer detection in general is high and has helped to increase the survival rate for breast cancer (see reference 3). However, in females with dense breasts, the sensitivity declines to near 62% (see reference 4). Biopsy is routinely done under conventional US guidance; however, about 76% of biopsies performed yield a benign result (see reference 5). Biopsy is an invasive procedure and to reduce the necessity for performing it, ultrasound elastography was proposed. Generally speaking, cancer tissues are stiffer than the adjacent normal tissues (see references 6-8), due to their higher cell density than the surrounding normal tissue (see reference 9). This characteristic feature made elastography a powerful technique for cancer detection, as a quantitative stiffness contrast visualizing technique, which would decrease the number of unnecessary biopsies (see references 6-8).

Elastography provides an insight into the elastic properties of biological tissues by calculating tissue displacements and estimating tissue strains (see references 10, 11). A considerable dynamic range of the estimated strains is expected due to the inherent tissue heterogeneity, wherein tissue with higher stiffness would generally experience lower strain values than those with lower stiffness. Visualizing the differences in tissue stiffness is a key characteristic for cancer diagnosis (see reference 12).

Elastography was first reported by Ophir et al. (see references 13, 14). Basically, the technique is used to calculate small displacements between consecutive ultrasound image pairs that are acquired under quasi-static axial compression. Cross-correlation between pre- and post-compression frames is employed to estimate tissue displacements, which in turn are used to calculate tissue strains and produce elastograms. Different approaches have been described in the literature (see references 12, and 15-20) to estimate time delays between the corresponding ultrasound frames, and hence local tissue displacements.

Three dimensional (3D) elastographic volumes are more informative as they present better qualitative and quantitative measures of the size and shape of breast masses. 3D elastography has been recently addressed by a number of authors. Bharat et al. (see reference 21) presented 3D constructed elastographic volumes for a tissue mimicking phantom of a canine liver with created thermal lesion in vitro. Manual segmentation was used to isolate the lesions from the elastograms and construct the lesions' shapes in 3D. 3D axial strain map was developed by Deprez et al. (see reference 22) for a pressure ulcer-mimicking phantom using an iterative constrained optimization process to estimate the axial strains. However, their study did not include quantitative assessments. Treece et al. (see reference 23) and Housden et al. (see reference 11) presented another study using freehand ultrasound elastography with a 3D probe. 3D slices of elastograms were constructed for a number of phantoms, including agar phantom and a breast biopsy phantom. No quantitative parameters were performed in this study.

Elastography classification of breast masses as benign or malignant primarily depends on two parameters (see references 6, and 24-29). The first parameter is the relative size of the mass imaged with elastography and B-mode ultrasound (see reference 24). It was observed that malignant masses appear bigger in the elastograms than in B-mode images. The second parameter is the strain ratio of the mass with respect to the surrounding soft tissue. This parameter uses the fact that malignant masses are stiffer than benign ones (see reference 30). One difficulty with this parameter is that an overlap exists in the strain ratio values between benign and malignant cases, and in some cases it is hard to diagnose the mass.

Several studies applied a viscoelastic model for characterizing human tissues. Emelianov et al. (see reference 31) used elasticity imaging for estimating nonlinear tissue elasticity in vitro using a canine kidney. Xu et al. (see reference 32) reported a method to characterize the edematous tissue in rats and to make a distinction between fibroses and inflammation in vivo. One research group (see references 33 and 34) used a time series of strain images in vivo and computed viscous creep curves to estimate a strain retardance time parameter that provided discrimination between malignant and benign breast tumors. Oberai et al. (see reference 35) applied a nonlinear hyperelastic model of the breast tissue in vivo to estimate three nonlinear metrics describing the tissue behavior.

However, few recent studies applied a viscoelastic classification model for breast masses using elastography. Using mechanical measurements in vitro, an exponential stress-strain relationship was measured for a number of breast tissues, including fat, glandular and fibrous tissues, and malignant masses; ductal carcinoma and invasive ductal carcinoma (see references 8, 30, and 36). In general, malignant masses exhibit a stronger nonlinearity than that observed for benign masses and the surrounding healthy tissue. Since the modulus of elasticity for a mass is a strain dependent parameter, the higher the strain level the stiffer the tissue becomes (see reference 8). This nonlinear behavior of malignant and benign masses is employed in the present invention to classify breast masses under different compression levels in vivo.

Most previous elastography studies were concerned with axial strain imaging, which is one of the independent strain components that describe deformation of a material. Axial shear strain is another independent strain component to be feasible for elastographic imaging, which was reported by Ophir and his co-authors (see references 37-40). An independent study by Xu et al. (see references 41) used normalized axial shear strain area (NASSA) to classify in vivo cases, and suggested the axial shear strain imaging to complement axial strain and B-mode imaging in classifying breast masses. Thittai et al. (see reference 42) investigated the potential of NASSA feature on a large in vivo dataset and concluded that this strain imaging type may be added to the existing routine clinical practices.

In the present invention, the acquired ultrasound RF data were used to construct elastography images and volumes that represent internal relative strains of the compressed tissue. The present method was tested in vitro on a breast phantom, then applied in vivo. An integrated mammography-ultrasound system was utilized in the acquisition of RF data in vivo, as well as applying tissue compression. A modified one dimensional time-domain estimator using normalized cross correlation technique was used to construct elastographic images of the breast lesion. The lesions represented by stiff areas in the elastograms were chosen for further quantitative analysis and characterization. Strain difference values between the mass and the surrounding soft tissues were estimated at different compression levels. Curve fitting was then applied on the resultant data using a power stress-strain relationship. The nonlinear parameter describing this relationship was used as a classification feature to judge the malignancy of the lesion. This preset invention's method classifies the mass type more accurately and characterizes it when the strain ratio measure fails because of the overlap between malignant and benign masses stiffness values.

The present method was used to calculate different strain types and use them to construct new forms of 3D elastography volumes. The constructed volumes included axial, first principal, maximum shear and Von Mises strains. The last three types of elastographic volumes incorporated the normal axial strain and axial shear strain together, which provided better distinction of the stiff mass from the soft tissue. The present invention's elastographic methods can be used as a powerful noninvasive quantitative characterization tool for breast cancer, with the capability of visualizing and separating the masses in a three-dimensional space. This results in reducing the need for biopsy to determine the malignancy or benignancy of breast masses.

The algorithm used to produce the elasticity images; elastograms, was based on the standard time-domain estimator (TDE) using normalized cross-correlation that calculates displacements of the tissue under compression (see references 10-14, 16, 43, and 44). A gradient operator is then applied to estimate strain components that form the elastograms. A constitution of co-registered multiple elastograms can be used to construct a three dimensional elastography volume. A research grade ultrasound unit (Sonix RP, Ultrasonix Medical Corporation, Richmond, BC, Canada) was used to acquire radiofrequency (RF) signals. Tissue compression was carried out using a motorized positioning system for the in vitro experiments and a modified mammography stage for the in vivo studies. Volumetric raw RF data were acquired using a 3D mechanically swept ultrasound sector probe operating at 9 MHz frequency. A stepper motor is used to rotate a one dimensional array of 128 transducer elements to render 3D volumes, as shown in FIG. 1. Each acquired volume consists of a total number of 40 slices, with an inter slice spacing of 1.462 degrees, and a total field of view of 58.5 degrees. Pre- and post-compression volumes were acquired to produce a 3D elastogram, which was constructed based on slice by slice calculations.

Figure 2:
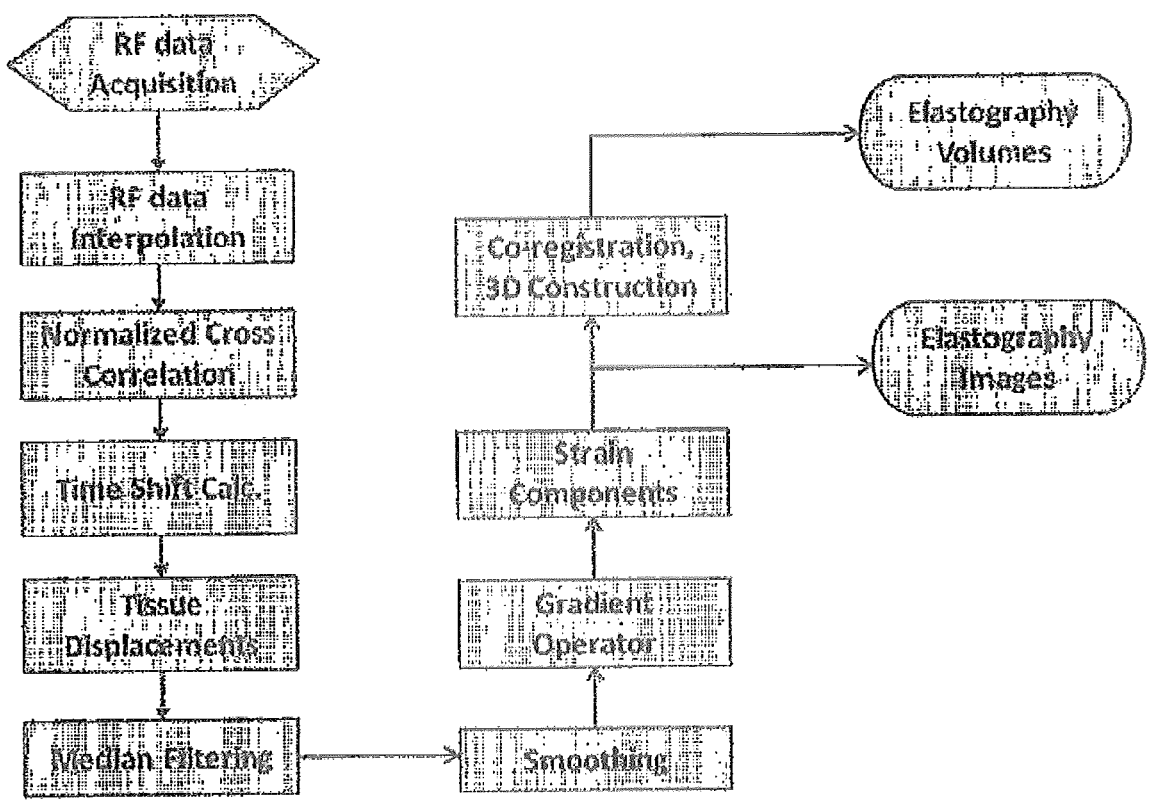
FIG. 2 Sets forth an elastography signal processing flowchart of the method of the present invention.

The present method using elastography started with acquiring the pre-compression raw volumetric RF data of the tissue under investigation using the ultrasound scanner. The breast tissue was compressed at a ratio of about 1% of its initial thickness, and the RF data were acquired during the post-compression stage. The ratio of 1% ensures to give good quality elastograms with a reasonable amount of noise [40]. The noise mainly resulted from local de-correlations between pre- and post-compression frames due to tissue deformation, so a moderate amount of compression was used to compensate between contrast and noise levels. A modified TDE technique (see references 13, 14, and 16) was used to calculate time delays of the RF data. This technique is based on one dimensional displacement estimation analysis, i.e. along RF line samples. The flowchart describing the method and RF signal processing is illustrated in FIG. 2.

RF data normally consist of a number of lines that is equal to the number of ultrasound scan lines, which form the horizontal axis of the ultrasound image. Each acquired ultrasonic RF line is divided into a number of windows, in which a single window consists of a number of RF samples. The used window size was about 1.6 mm with a window overlap of 75%. A cubic spline sample interpolation with a ratio of 20:1 was applied on individual windows, to increase the displacement estimation resolution and to smooth the RF curves before the cross-correlation step. The interpolation process was found to be reducing the noise level. Then cross-correlation was calculated between pre-compression and post-compression RF windows, i.e. windows with the same index in two subsequent frames. The cross-correlation function was normalized to produce accurate time-delay estimates. Equation (1) was used to calculate the normalized cross correlation function [45]

$$R_{XY} = \frac{\sum_{i=1}^{W} X(i)Y(i)}{\sqrt{\sum_{i=1}^{W} X^2(i)} \sqrt{\sum_{i=1}^{W} Y^2(i)}}, \quad (1)$$

where $R_{XY}$ is the correlation function, X and Y the pre- and post-compressions RF signals respectively, W window length and i an index pointing to the signal samples. The location of the peak of the cross-correlation function was determined, which corresponds to the local time delay between pre- and post-tissue compression windows. This estimated time delay is proportional to the local tissue displacement.

Cross-correlation false peaks usually occur when a secondary peak exceeds the true peak. They appear as dots or "black and white pepper noise" in the displacement images, and can be reduced with the use of a suitable median filter (see references 16, 44, and 46), which was used in this invention. Then a cubic smoothing spline function was applied on the tissue displacement image to reduce the effects of the remaining noise and to make the displacement profile more uniform and even.

The strain values are functions of the estimated displacements' derivatives. To calculate the strains from tissue displacements the gradient operator was applied as follows:

$$\varepsilon_y = \frac{\partial v}{\partial y}, \gamma_{xy} = \frac{\partial v}{\partial x}, \quad (2)$$

where v is the displacement estimate in the axial direction, $\varepsilon_y$ the normal axial strain, and the axial shear strain.

The conventionally used strain component in elastography imaging is the normal axial strain, as it provides direct information about tissue stiffness. Recently, axial shear strain received special research attention, as it was hypothesized that it provides some information about the bonding near the boundary between stiff and soft tissues (see references 38, 40-42, and 47). Both axial normal and shear strain components are independent components of the complete strain tensor that fully describes the mechanical behavior of the tissue.

Other derived useful strains can be calculated based on both normal axial strain and axial shear strain. The new derived strains are: first principal strain, maximum shear strain and Von Mises strain. The relations defining these strains are:

$$\varepsilon_1 = \frac{\varepsilon_y}{2} + \sqrt{\left(\frac{\varepsilon_y}{2}\right)^2 + \left(\frac{\gamma_{xy}}{2}\right)^2}, \quad (3)$$

$$\varepsilon_2 = \frac{\varepsilon_y}{2} - \sqrt{\left(\frac{\varepsilon_y}{2}\right)^2 + \left(\frac{\gamma_{xy}}{2}\right)^2},$$

$$\gamma_{max} = 2\sqrt{\left(\frac{\varepsilon_y}{2}\right)^2 + \left(\frac{\gamma_{xy}}{2}\right)^2},$$

-continued $$VM = \sqrt{\frac{3}{2}(\varepsilon_1^2 + \varepsilon_2^2) - \varepsilon_1 \varepsilon_2},$$

where $\epsilon_1$, $\epsilon_2$ are the first and second principal strains respectively, $\gamma_{max}$ the maximum shear strain, and VM the Von Mises strain. We may refer to the first principal, maximum shear and Von Mises strains as derived strains, because they were originally calculated from the normal axial strain and axial shear strains.

The derived strains incorporate information regarding both tissue stiffness and boundary bonding between soft and stiff tissues, with varying degree according to the strain type used. We will show in the results section that they can provide an enhanced boundary between the lesion and the surrounding soft tissue, especially the maximum shear elastogram. This can be very useful in facilitating an automated segmentation process of the lesion, and also for more accurate lesion volume calculations.

The other displacement component, lateral displacement u can also be estimated, but it is very noisy compared to the axial displacement. This is a fundamental limitation with any ultrasound system due to suboptimal sampling between the RF lines, which affects elastography and B-mode imaging as well (see references 40 and 48). It should be noted that the present inventors have neglected the lateral components from the calculations, due to its noisy nature.

3D Elastography In Vitro

Figure 3:
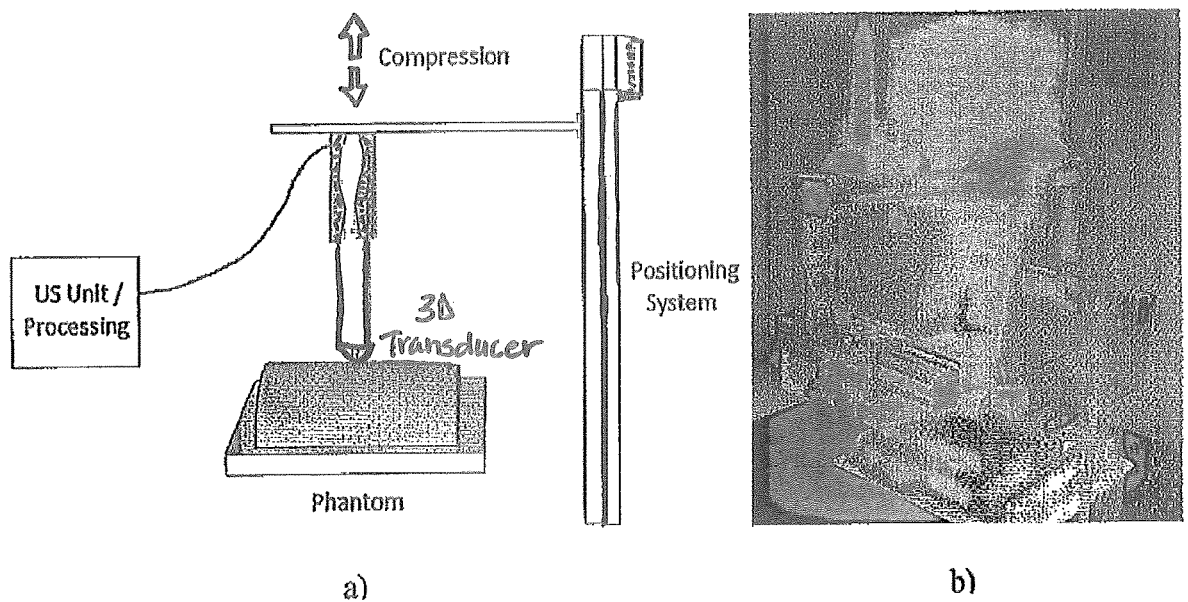
FIG. 3 Shows a preferred embodiment of the device of the present invention comprising a positioning system for raising or lowering the vertical position of a 3D transducer (and optionally providing for the horizontal movement (right to left positioning)) of the 3D transducer) wherein the 3D transducer is in juxtaposition to and preferably in communication with the positioning system (more preferably wherein the 3D transducer is attached to the positioning system), a US (ultrasound) unit and computer processor in communication with the 3D transducer, and a compression device (not shown in 3(a) view) for supplying compression of the tissue to be examined:
   a) In lab: on a breast tissue phantom,
   b) In clinic: with a mammography paddle of the present invention for delivering compression to a tissue to be examined, and including an added (optional) holder for the 3D ultrasound transducer (probe).

In vitro experiments were conducted on a breast elastography phantom (CIRS, Norfolk, Va., USA) to test the elastography scheme presented in FIG. 2. The phantom simulates, in both shape and size, a patient's breast in the supine position. It consists of a soft elastic material that encloses 13 randomly positioned stiff inclusions. Each inclusion is three times stiffer than the surrounding soft material. The inclusions are spherical in shape with diameters ranging from 2 to 10 mm. Imaging parameters such as window length, window overlap, compression level, and interpolation ratio were evaluated using the in vitro phantom study. The experiment setup is sketched in FIG. 3.

Compression was performed using a motorized positioning system coupled to the ultrasound probe. The positioning system facilitated compression with precise levels in steps of 250 μm. We found that a compression of 500 μm (about 1% of the total height of the phantom) provides the best image signal to noise performance, consistent with those reported in the literature (see references 14, 24, 40, and 48).

Please note that raw RF data were exploited first in the strain estimation process without scan conversion, then scan conversion operations were performed to display displacement and strain images in the correct sector shape. Then another scan conversion operation was applied on the co-registered slices in the elevational direction, to construct the correct sector 3D elastography volumes.

Using a sector transducer for elastography, the actual estimated displacements are the radial and angular displacements because of the geometry of the probe. Yet, a transformation from polar coordinates to Cartesian coordinates, similar to the one reported by Chen et al. (see reference 18), was performed to obtain the axial component of the displacement. The resulting normal axial strain and axial shear strain were estimated using Eq. 2 based on the axial displacement.

3D Elastography In Vivo

An in vivo study was conducted on ten volunteer patients at the Betty Puskar Breast Care Center, West Virginia University. The patient's age range was 39 to 65 years. The patients were diagnosed with having palpable or non-palpable breast masses, using mammography imaging modality. They were recruited for this study, followed by a biopsy on the same day to confirm the study outcomes. Independent diagnosis of the breast mass and its type (malignant or benign) using the proposed approach presented herein was compared with biopsy results for each patient.

Experimental Setup

The mammography machine located in the Betty Puskar Breast Care Center, West Virginia, USA, was chosen to be utilized. Its compression stage was used to perform elastography compression as well as to apply the three pre-compression levels necessary to apply the nonlinear mass classification process. Also, the stage of the compression unit was capable of measuring the applied tissue compression force, which is essential for the present invention, as will be discussed later in this section.

In order to couple the 3D ultrasound probe to the mammography compression stage, we designed a custom mammography compression paddle as described herein. The mammography paddles of the present invention are deformable rectangular plates mainly used for the application of the compression on the breast tissue while resting on a special holder. This pressure ensures homogeneity of the tissue during imaging, and decreases the breast thickness for more efficient X-ray penetration. The modified paddle is shown in FIG. 3(b). We added a movable fixture for the 3D ultrasound probe, with the flexibility of translating the probe in the X-Y plane to acquire images and volumes of the region of interest (ROI). Manual brakes were added to fix the probe in the required position. The fixture was made from aluminum, which makes it light weight and does not interfere with the pressure readings. The main consideration was to hold the probe so that it does not move, slip or rotate during the compression cycles, which ensures consistent acquisition of volumes. The fixture also allows for the ability of imaging using both ultrasound and mammography without replacing the plate, which is an additional advantage. The paddle has a slot opening, so that the ultrasound probe can have good contact with the breast tissue.

For each volunteer case, the experiment started with locating the suspected mass under conventional ultrasound, and then the breast was positioned under the modified mammography paddle, so that the ROI was directly under the ultrasound probe. An initial pre-compression was applied, volumetric RF data were acquired, then an additional small compression (an amount of about 1% of the breast thickness) followed for elastography to work, and the post-compression RF data were acquired. This cycle of the application of a pre-compression pressure followed by the elastography compression was repeated three times at three different pre-compression levels to obtain three elastographic volumes at each level for the purpose of mass classification. The three pre-compression levels were measured by the mammography stage having compression values of 2, 3 and 4 Kgf, respectively. The three pre-compression levels were similar to those currently used in mammography imaging. The upper limit of 4 Kgf was selected based on patient comfort, and to avoid any chance of pain due to excessive tissue compression.

Mass Classification

The stress-strain curves of the breast tissues, which describe the mechanical behavior of the tissue under different stresses, follow an exponential behavior with the malignant masses having a steeper curve than the benign one. These relationships were reported in vitro in previous studies using mechanical measurements techniques (see references 8, 30, and 36). The studies reported that tissue modulus is a strain dependent parameter, and the higher the strain level the stiffer the tissue becomes. Therefore, malignant masses become stiffer more rapidly than benign masses while increasing the applied stress.

Figure 4:
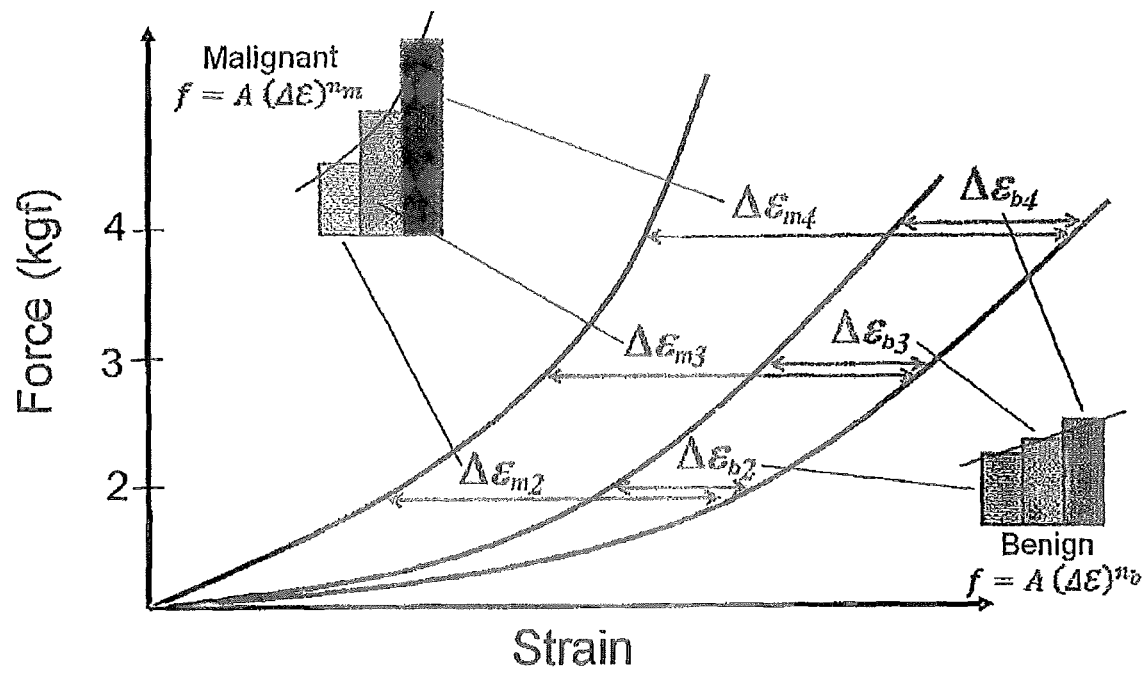
FIG. 4 Shows a graph that sets forth strain (x-axis) versus force (kgf) regarding the quantitative assessment of breast masses.

We believe that the strain difference between the suspected masses and surrounding healthy tissues becomes more significant at high compression levels. We also believe that the strain difference parameter is exponentially increasing with the applied stress. This behavior is more pronounced for malignant tissues since they exhibit strong nonlinear stress-strain behavior. We used this material nonlinearity to classify and characterize the mass type quantitatively and to differentiate between malignant and benign tissues, see FIG. 4. An approximate force-strain curve was plotted for each case and used to characterize the breast mass. The curve was drawn using three pre-compression force levels corresponding to 2, 3 and 4 Kgf, respectively. The force values were read directly from the mammography compression stage, and we considered them as being proportional to the true stress/pressure levels. The present inventions classification method can be presented with the following expressions:

If $\Delta\epsilon_{m4} \gg \Delta\epsilon_{m3} \gg \Delta\epsilon_{m2} \rightarrow$ Malignant behavior, Else If $\Delta\epsilon_{b4} \geq \Delta\epsilon_{b3} \geq \Delta\epsilon_{b2} \rightarrow$ Benign behavior, (4)

where $\Delta\epsilon_{mi}$ (i=1, 2, 3) corresponds to strain differences between the suspected malignant mass and the surrounding soft tissue at three pre-compression levels, and $\Delta\epsilon_{bi}$ (i=1, 2, 3) are for a suspected benign mass.

We believe that malignant masses exhibit stronger nonlinearity than that observed for the benign masses. This behavior was also clearly observed in the strain difference values between the masses and the surrounding healthy tissues. To quantify the degree of mass nonlinearity, an empirical power relationship between force and strain differences was used. Curve fitting was applied on the estimated data using this power relationship to describe the change in degree of the strain differences with the multi-compression levels. Equation 5 describes the nonlinear elastic power law behavior as (see reference 49):

$$f = A(\Delta\epsilon)^n \quad (5)$$

where f is the applied force level, $\Delta\epsilon$ is the strain difference between the suspected breast mass and surrounding healthy soft tissues. A and n are generalized fitting parameters, where n was considered to be the main nonlinear parameter characterizing the breast mass type. The subscripts m and b in FIG. 4 denote malignant and benign, respectively. This parameter was calculated for all cases involved in the study to estimate the threshold value that discriminates between the benign and the malignant masses. Note that the applied elastography compression was about 1% of the initial thickness of the breast tissue at every compression level. This was again to compromise between image quality and noise.

In summary, to achieve this in reality, a pre-compression pressure was applied on the breast tissue at three different levels. At each level an additional elastography compression was applied and the scheme in FIG. 2 was followed to estimate strains and produce elastography images and volumes at that specific level.

As mentioned earlier, the relative size of the mass between elastograms and B-mode images is commonly used as a classification parameter. Usually, length or area measurements are used. Using 3D imaging, volume calculations were feasible. As a result, we used the relative estimated volumes as an additional mass classification parameter. Volume calculations were performed by calculating the summation of mass' areas in each slice constituting the elastographic/B-mode volume. Manual segmentation was used to obtain the area of the mass in each slice. If the ratio between both volumes had a value bigger than one, this indicates malignancy, otherwise the mass is considered to be benign.

Results

In this section, qualitative and quantitative results are presented in vitro and in vivo. Different breast mass classification techniques are presented and compared with the new nonlinear parameter obtained from multi-compression elastography of the present invention. 3D image constructions of the new derived strains are also presented.

Elastography In Vitro

Figure 5:
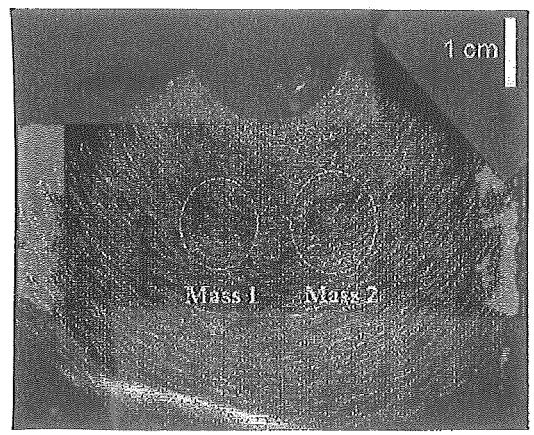
FIG. 5 Shows breast phantom imaging:
   a) conventional B-mode ultrasound image.
   b) 3D axial strain elastography, where the two inclusions are very evident.
Figure 5:
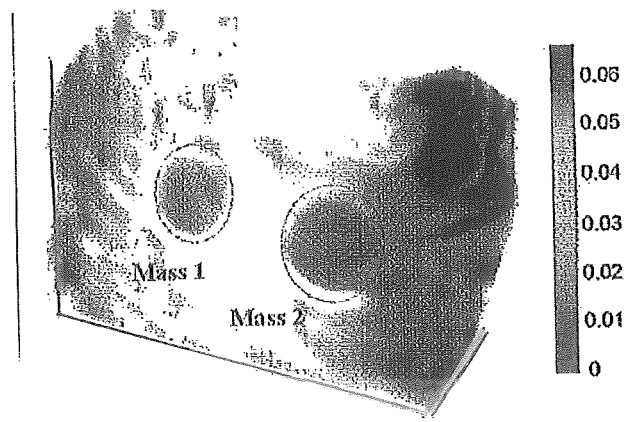

The scheme described in FIG. 2 has been applied on the breast phantom using motorized compression with a positioning system. The B-mode image and 3D normal axial elastogram are shown in FIG. 5. A transparency degree was applied to the constructed volume shown in FIG. 5(b) to show the two inclusions located inside the volume. Transparency hides the high strain voxel values and shows only the low strain voxels, according to a threshold determined interactively. Therefore, only the stiff inclusions are displayed along with parts of the tissue that exhibited low axial strain values. The inclusions were barely seen in the B-mode image, yet in the accompanying elastographic volume the inclusions were identified clearly from the soft background, with the appearance of nearly perfect spheres, which was the actual shape of the inclusions. This emphasized the efficacy of using 3D elastography in estimating the actual shape of the stiff masses. Furthermore, strain ratio of the inclusions showed an average value of about 3 times, which agreed well with the breast phantom manufacturer's specifications. Strain ratio was calculated as the ratio between the mean strain values of the soft and stiff tissues, respectively. The strain values were selected manually from the resultant elastograms, and the corresponding mean values were computed. Because this experiment was performed on a tissue mimicking phantom, no mass classification procedures were applied nor tested in this case.

In addition to the normal axial elastogram, the derived strains elastograms were constructed using Eq. (3), and shown in FIG. 6. The figure demonstrates the four 3D elastographic volumes with a cross sectional view of one inclusion. No transparency was applied on the constructed volumes in this case, because the purpose was to emphasis the boundary between the stiff and soft tissues, i.e. low and high strain regions. The strain values within the four volumes were normalized for a fair comparison.

Figure 6:
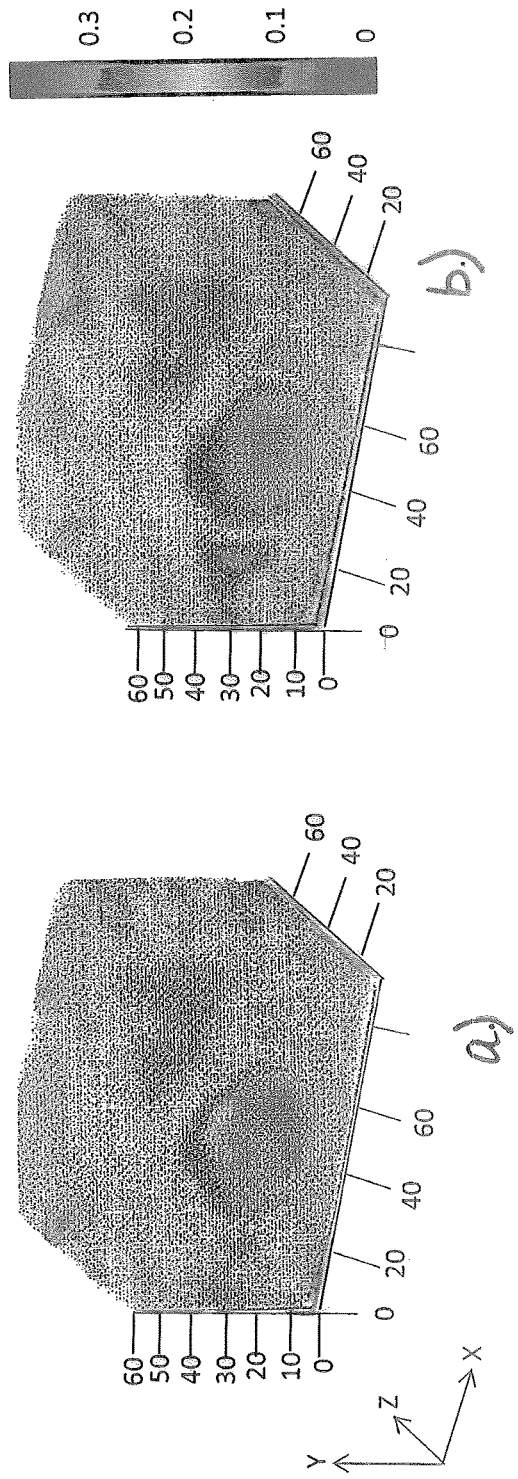
FIG. 6 Shows different strain elastograms:
   a) normal axial strain,
   b) first principal strain,
   c) Von Mises strain,
   d) maximum shear strain.
Figure 6:
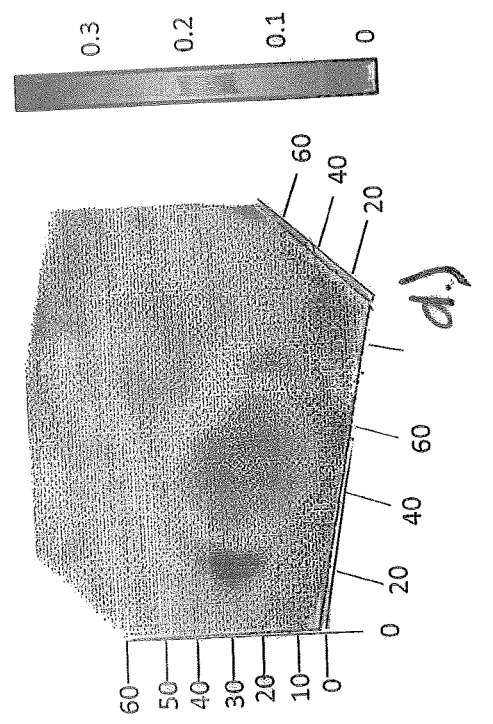
Figure 6:
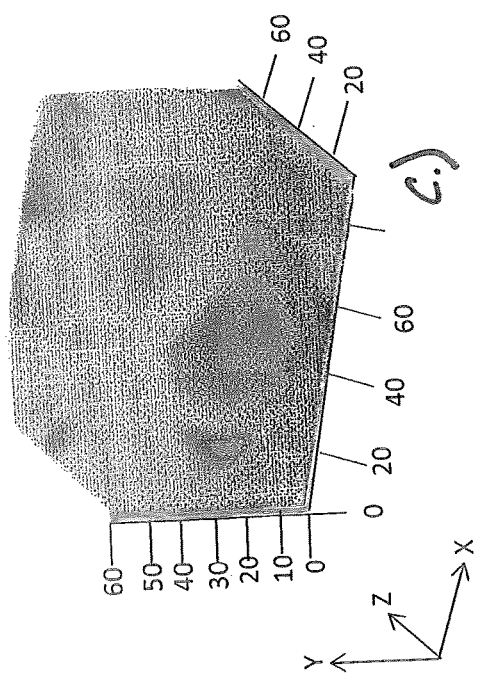

The derived elastographic volumes, FIGS. 6 (b-d), showed a degree of enhancement for the inclusion's boundary compared with the normal axial strain volume. This enhancement was most apparent in the maximum shear strain volume, FIG. 6(d) and the inclusion can be more easily isolated from the soft background. An important feature of this boundary enhancement is that it took place at an angle relative to the axial mechanical compression direction. This is a fundamental property of the shear strain during a uniaxial loading, where shear strains are maximum at slip planes of about 45 degrees. This would be useful to demarcate the boundaries of two dissimilar materials, as the case for a stiff mass surrounded by healthy tissues.

Phantom inclusion volume calculations were performed by summing the mass' areas in individual slices forming the 3D volumes for the derived strains. The volume calculations are listed in Table 1 (FIG. 15), along with the associated error and the estimated inclusion radius. The actual inclusion's diameter of 9 mm was measured using B-mode imaging, and this measurement was confirmed by the listed inclusion sizes in the manufactures specifications. The estimated radius values listed in Table 1 (FIG. 15) are calculated based on the measured volumes, and they were not measured directly from the corresponding elastograms. It was observed that the measurements agreed well with the phantom's manufacturer specifications regarding the inclusion size. As a result, it was proven that the inclusion's volume is preserved in all of the derived strain volumes.

Elastography In Vivo

Figure 7:
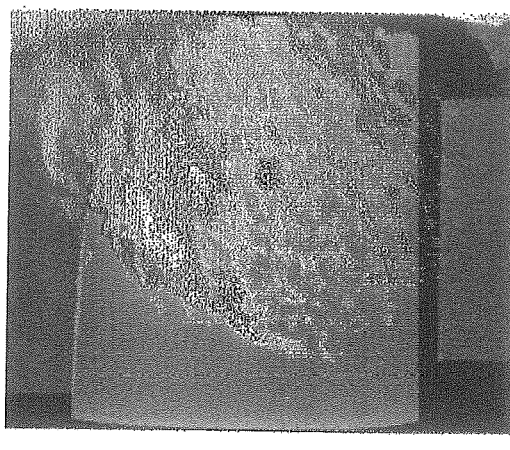
FIG. 7 Shows benign breast mass:
a) conventional ultrasound,
b) mammography,
c) elastography image
d) elastography volume.
Figure 7:
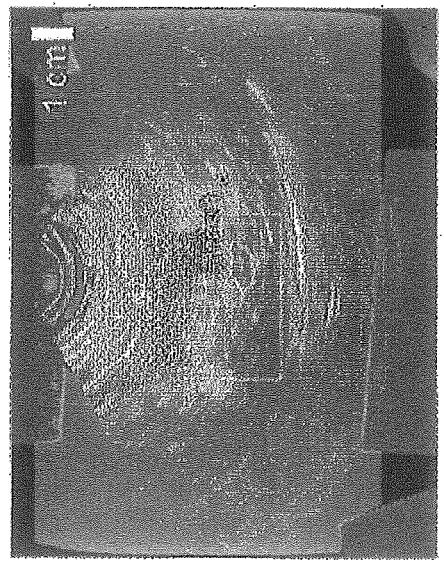
Figure 7:
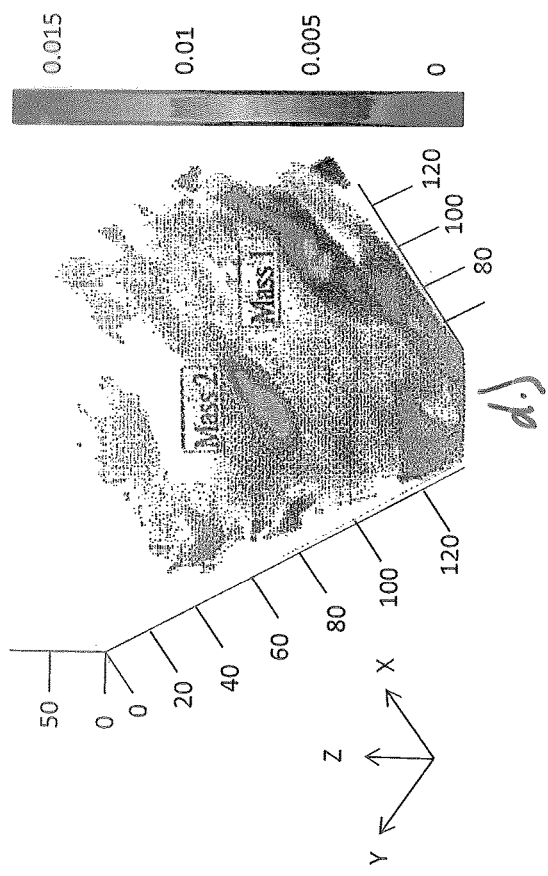
Figure 7:
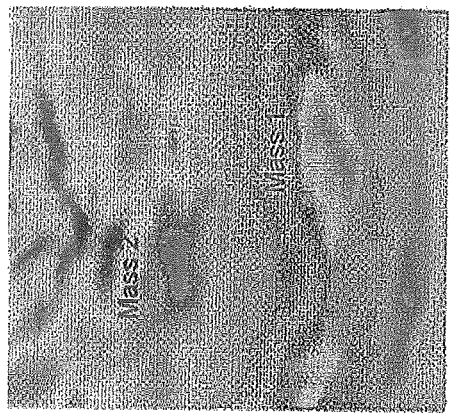

3D Imaging:

After gaining insight of the 3D elasticity imaging techniques in vitro, an in vivo study followed. Ten volunteer patients with pre-detected masses using mammography were included in the study. The same ultrasound system mentioned in section 2 was used for RF data acquisition. Two cases were excluded from the analysis. One case had the mass on the edge of the breast, and it was very difficult to acquire useful elasticity images for this case. The other case had a small breast size, so it was not possible to obtain elasticity images at different pre-compression levels. The remaining eight cases were diagnosed as three malignant and five benign breast masses. Malignant masses were classified using biopsy as two invasive ductal carcinomas and one invasive lobular carcinoma. The benign masses were two fibroadenoma, two fibrocystic changes and one fibroadipose tissue. The modified mammography paddle of the present invention was used to hold the probe, and the scheme in FIG. 2 was applied on the acquired RF volumetric data. FIG. 7 shows a benign lesion case imaged using ultrasound, mammography and elastography. Mammography imaging detected multiple well-circumscribed masses in the breast with a palpable mass at 8:00 that was reported to be increasing in size by the patient. The targeted mass for biopsy was marked as mass number 1 on the mammography and ultrasound images, where the mass had a hypoechoic nature on ultrasound. The appropriate region of interest (ROI) was marked as a yellow rectangle on the ultrasound image. 2D and 3D elastography showed the target mass; referred to as mass 1, along with another mass; mass 2. Both were stiffer than the background soft tissue. In 3D elastography, the outline of the masses was obvious, and each mass had an ellipsoidal shape. Furthermore, strain ratio of the target mass showed an average value of about 2.85 times stiffer than the background soft tissue.

Figure 8:
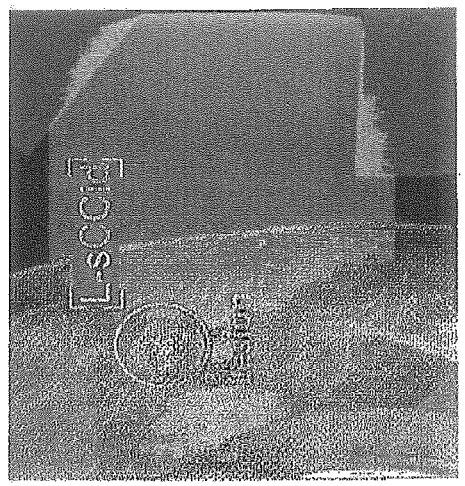
FIG. 8 Shows malignant breast mass:
a) conventional ultrasound,
b) mammography,
c) elastography image
d) elastography volume.
Figure 8:
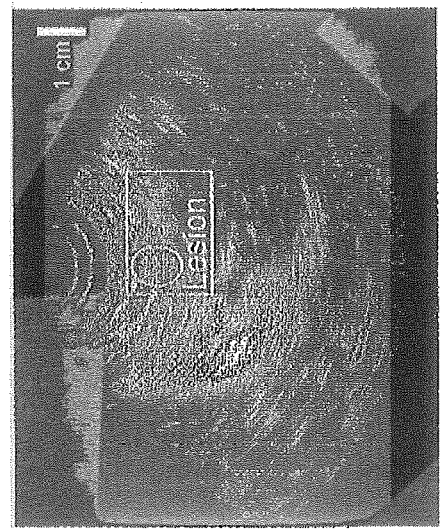
Figure 8:
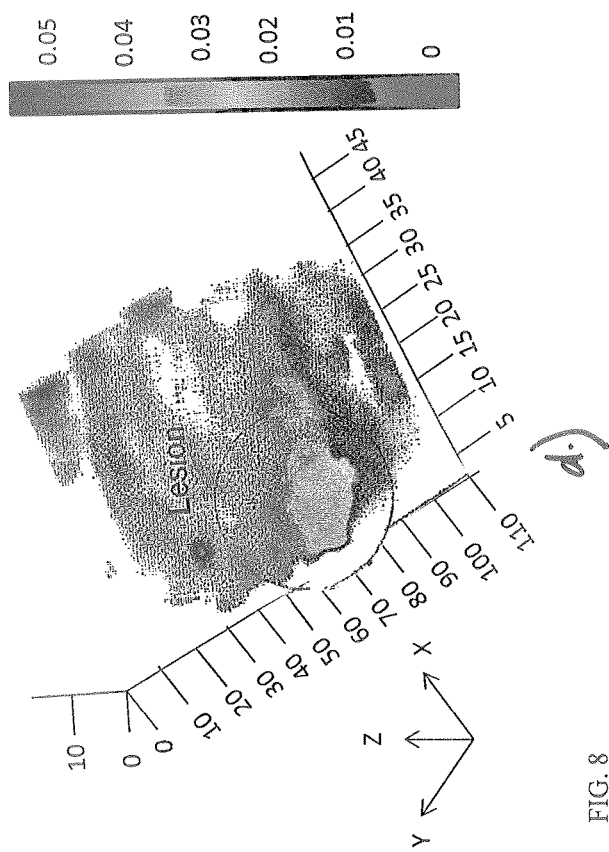
Figure 8:
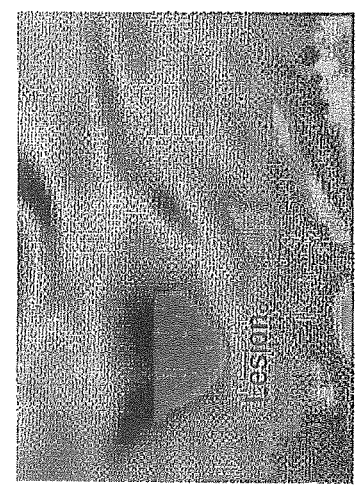

FIG. 8 shows a malignant case that was imaged using the three modalities. The mass is marked as lesion in all modalities in the figure. Mammography imaging showed the palpable mass at 11:00 to correspond to an irregular tumor. Conventional ultrasound revealed a solid, hypoechoic mass. The appropriate region of interest (ROI) was marked with a yellow rectangle on the ultrasound image. 2D and 3D elastography showed the targeted mass. In 3D elastography, the outline of the mass was obvious and it had an elongated spherical shape. Furthermore, strain ratio of the target mass showed an average value of about 6.3 times stiffer than the background soft tissue for this case.

Figure 9:
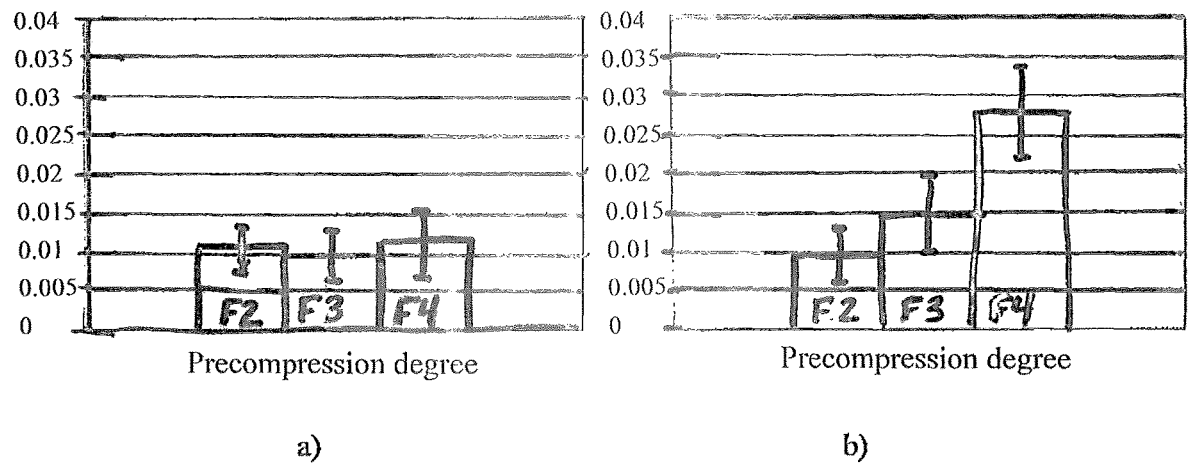
FIG. 9 Shows quantitative assessment using strain differences:
a) benign case,
b) malignant case.

Tissue Characterization:

A. Tissue Nonlinearity—Power Law:

Strain differences between stiff and soft tissues, were computed over the three pre-compression levels and plotted in FIG. 9 for benign and malignant cases, respectively. The computations were based on slice by slice calculations, in which each slice containing the target mass was used to calculate strain values, along with those of the surrounding soft tissue. The mean values, along with standard deviations for the whole volume, were plotted at each pre-compression level. Care was taken to select regions at the same imaging depth, so that both stiff and soft regions would be subjected to nearly the same stress level. Applying Eq. 4, FIG. 9(a) indicated a benign mass that follows a force-strain relationship similar to the normal tissue, but with shifted strain values. The classification of the mass being benign was confirmed by the biopsy results, which revealed a diagnosis of benign fibroadenoma. FIG. 9(b) indicated a malignant case in which the mass followed a steep force-strain relationship with respect to the normal tissue, due to the high stiffness of the malignant mass. The classification of the mass being malignant was also confirmed by the biopsy results, which revealed a diagnosis of invasive ductal carcinoma for this case. The plots showed good agreement with the proposed hypotheses, in which the strain differences values stayed nearly at the same level for the three pre-compression levels for the benign case, yet the values increased significantly for the malignant case. For all cases involved in the study, the overall average strain differences values were 0.011±0.005 and 0.018±0.014 for benign and malignant masses at different compression levels, respectively. Although those values do not provide a clear classification boundary between mass types, individual case analysis of the strain difference curve versus the applied force provided a very useful classifier. That classifier is the estimated nonlinear parameter.

Figure 10:
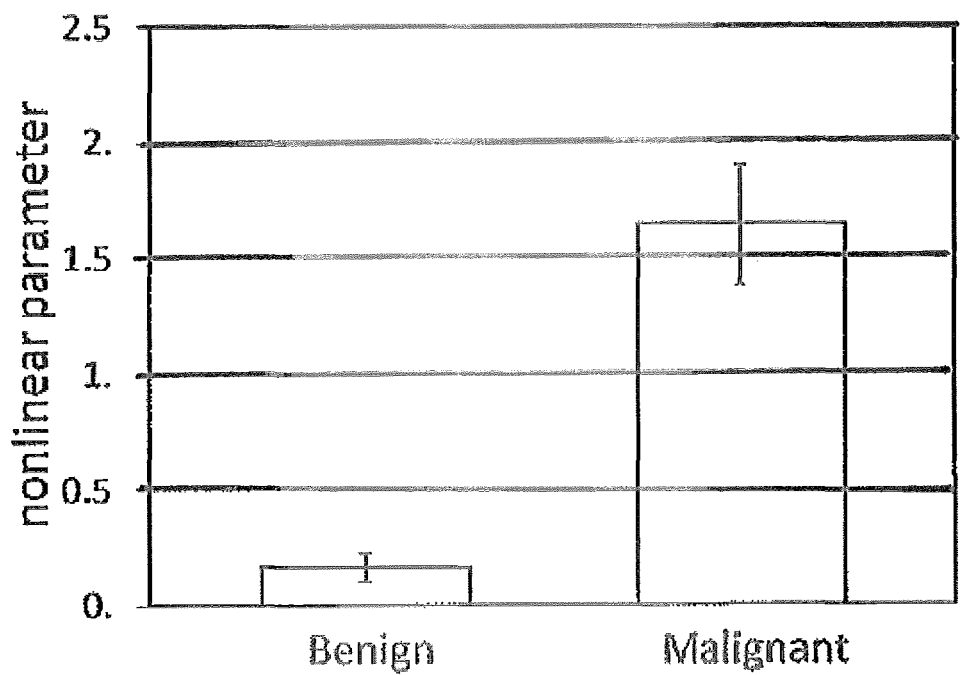
FIG. 10 Shows nonlinear parameter (n) estimated for all cases.

Equation 5 was used to fit the strain differences values using the power law. The nonlinear parameter n was then calculated for all volunteer cases. The overall average parameter value was 0.163±0.063 and 1.642±0.261 for benign and malignant masses, respectively. The accumulated values for each mass type are shown in FIG. 10. A significant differentiation between mass types using this parameter is obvious in the figure, in which malignant cases exhibited values of more than one, and benign cases had values of much less than one. These initial results suggested that using the new nonlinear parameter would be very helpful for differentiating between benign and malignant masses noninvasively using elastography.

Figure 11:
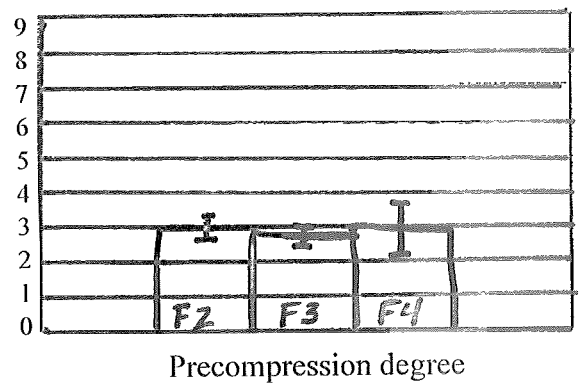
FIG. 11 Shows quantitative assessment using strain ratios:
a) benign case,
b) malignant case.
Figure 11:
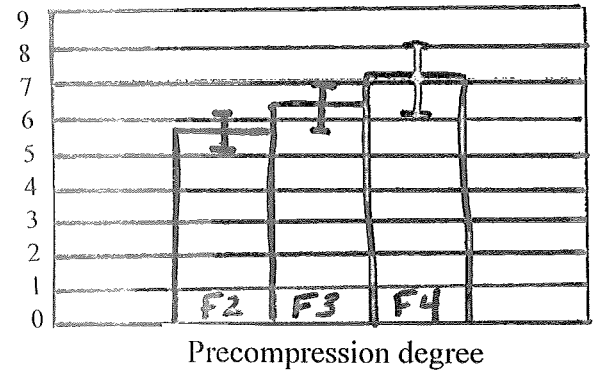

B. Strain Ratio:

Strain ratio between soft and stiff tissues was computed over the three pre-compression levels and plotted in FIG. 11 for benign and malignant cases, respectively. The computations were also based on slice by slice calculations, in which each slice containing the mass was used to calculate a single strain ratio value. The mean values, along with standard deviations for the whole volume, were plotted at each pre-compression level. Comparing FIG. 11 with FIG. 9, we observed the similarity in behavior between the strain ratios and strain differences curves. FIG. 11(a) shows that the strain ratio did not increase significantly for the benign case with an average value of 2.85 times. FIG. 11(b) shows a gradual increase in the strain ratio value with the pre-compression pressure for a malignant case, with an average value of 6.3. For all in vivo cases, strain ratio values for the benign and malignant masses had an average value of 2.135±0.707 and 4.21±2.108, respectively. Those average values agree with previously reported values for benign and malignant masses, in which a threshold value of 4.8 was considered (see reference 29).

Figure 12:
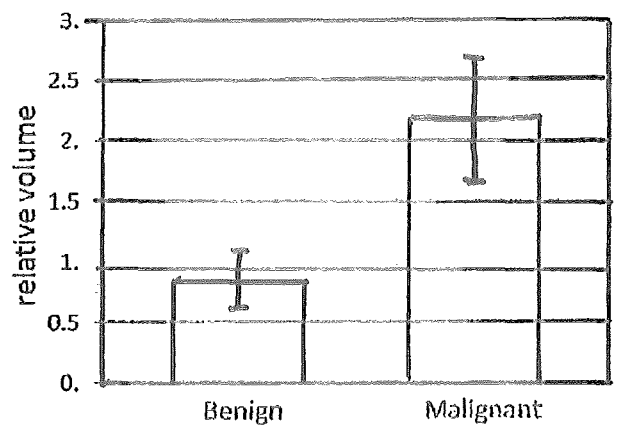
FIG. 12 Shows relative volume between elastograms and B-mode of breast masses estimated for all cases.

C. Relative Mass Volume:

As described in section 2, breast mass volume calculations for all volunteer cases were performed as the summation of mass's areas in the slices constituting the 3D elastographic/B-mode volumes. The accumulated relative mass volumes for each mass type category are shown in FIG. 12. Differentiation between mass types using this parameter is apparent in the figure, in which malignant cases exhibited values of more than one, and benign cases had values almost equal to one. The overall average relative mass volume values were 0.848±0.237 and 2.18±0.522 for benign and malignant masses, respectively.

Derived Strains Imaging

Figure 13:
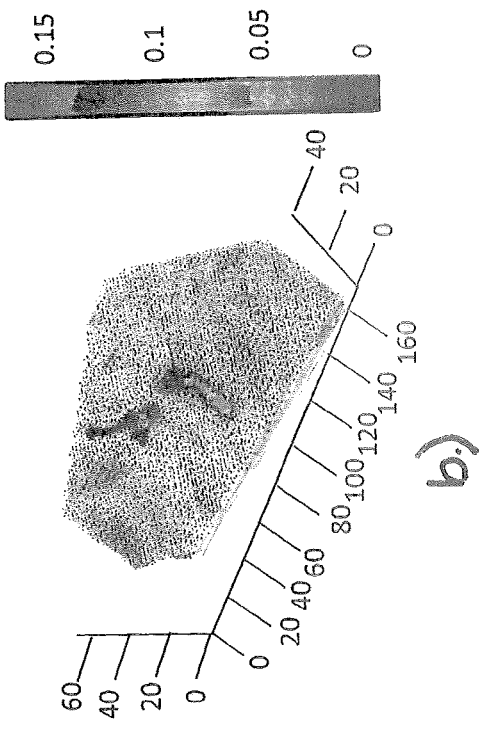
FIG. 13 Shows In vivo volumetric strain elastograms for a benign case:
a) normal axial strain,
b) first principal strain,
c) Von Mises strain
d) maximum shear strain FIG. 14 Shows In vivo volumetric strain elastograms for a malignant case:
a) normal axial
b) first principal strain,
c) Von Mises strain
d) maximum shear strain FIG. 15 Sets forth Table 1 that shows inclusion volume estimations for a breast phantom, as described herein.
Figure 13:
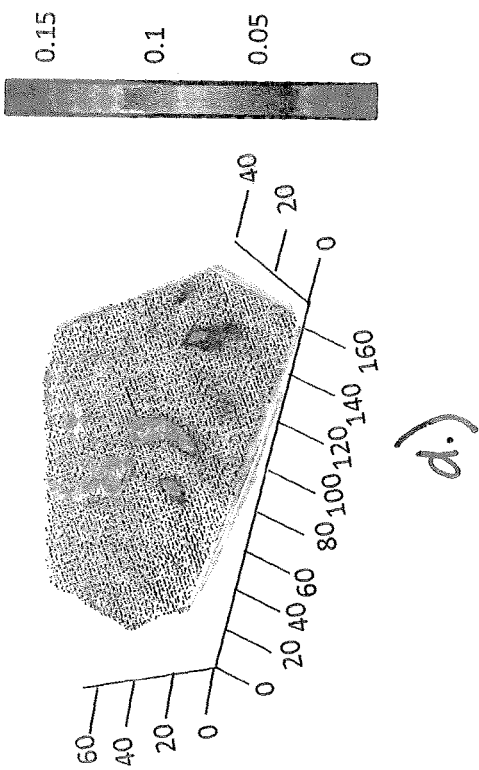
Figure 13:
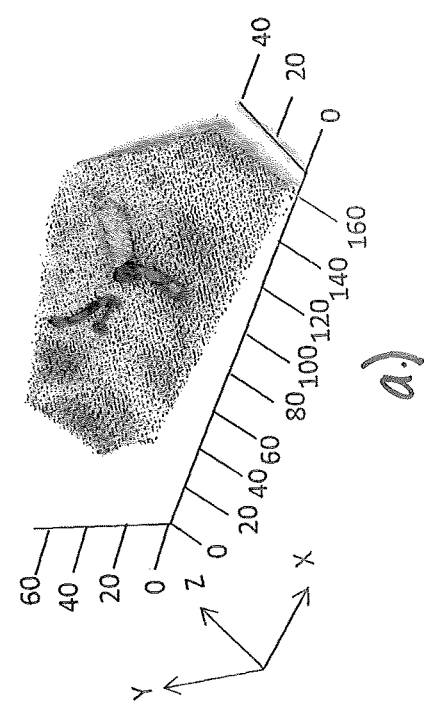
Figure 13:
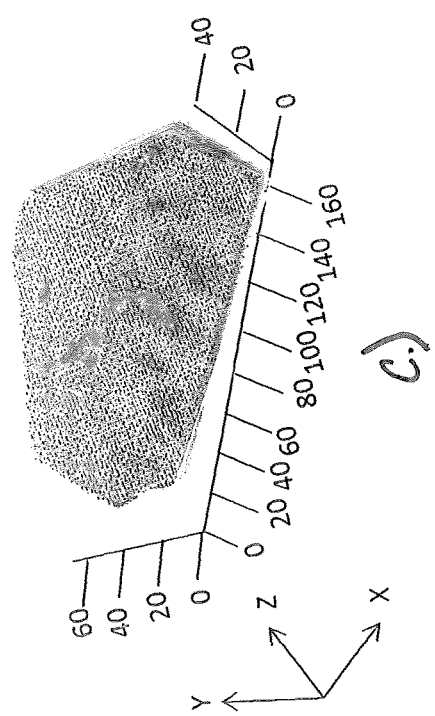
Figure 14:
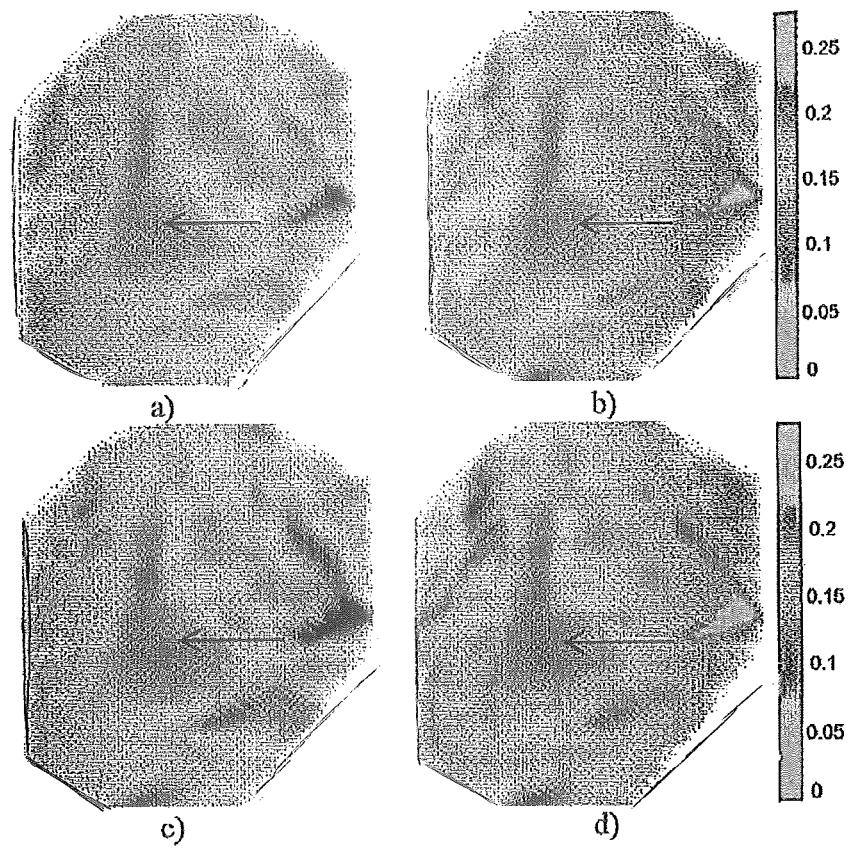
Figure 16:
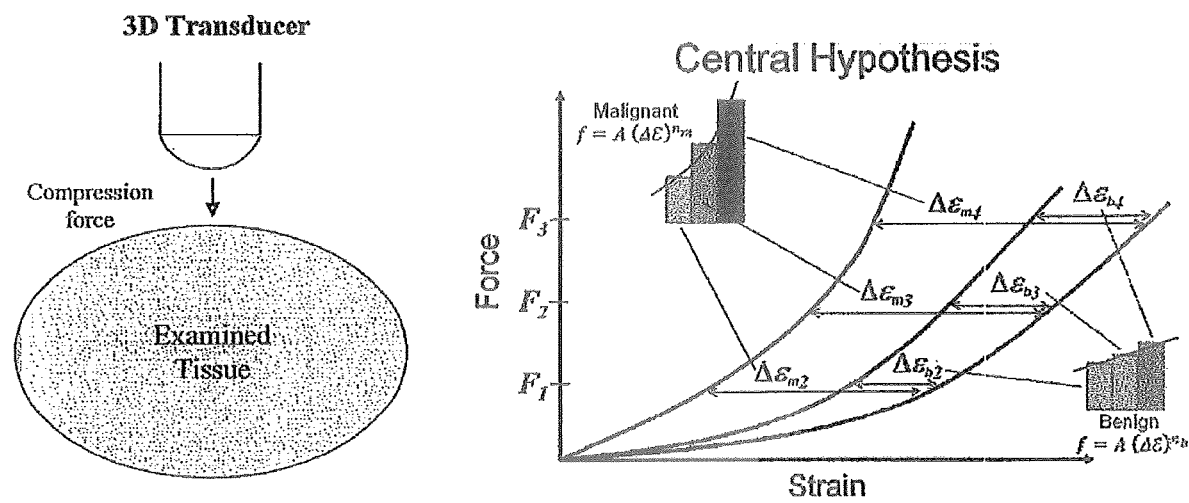
FIG. 16 Shows a preferred embodiment of the device of the present invention useful for breast examination (on the left) and a graph (on the right) that sets forth strain (x-axis) versus force (y-axis) and indicating malignant and benign conditions. The compression force set forth on the left of FIG. 16 may be applied with a moveable compression device that may optionally be motorized and capable of being controlled by a computer processor for applying various levels of compression against a tissue to be examined. The compression device may be for example a compression paddle as described herein. Preferably, the compression device is capable of applying successive levels of compression forces (F1, F2, F3, F4, and so on) against a tissue that is to be examined.
Figure 17:
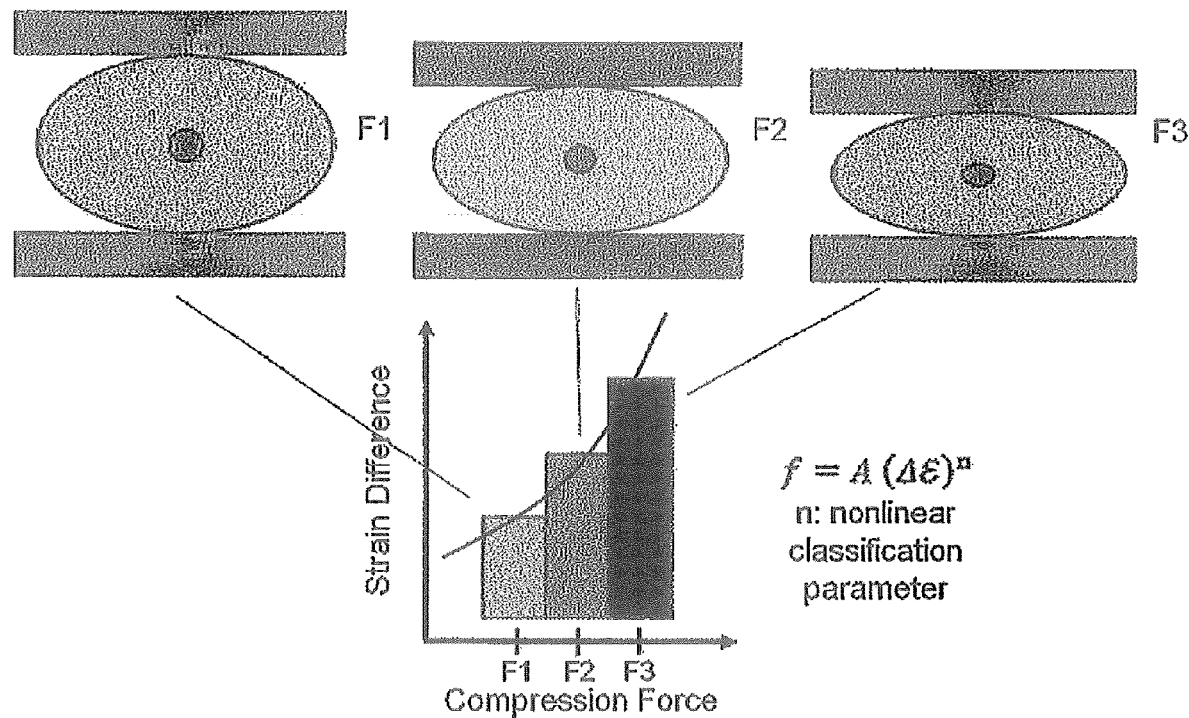
FIG. 17 Is a graph that sets forth compression forces (F1, F2, F3, and that additional compression forces may be utilized in the method of this invention as represented by the arrow pointing to the right making up the x-axis of the graph) accomplished with utilization of the device of the present invention on the x-axis versus Strain Difference (y-axis) obtained from use of a preferred embodiment of the nonlinear elastography method of the present invention.
Figure 18:
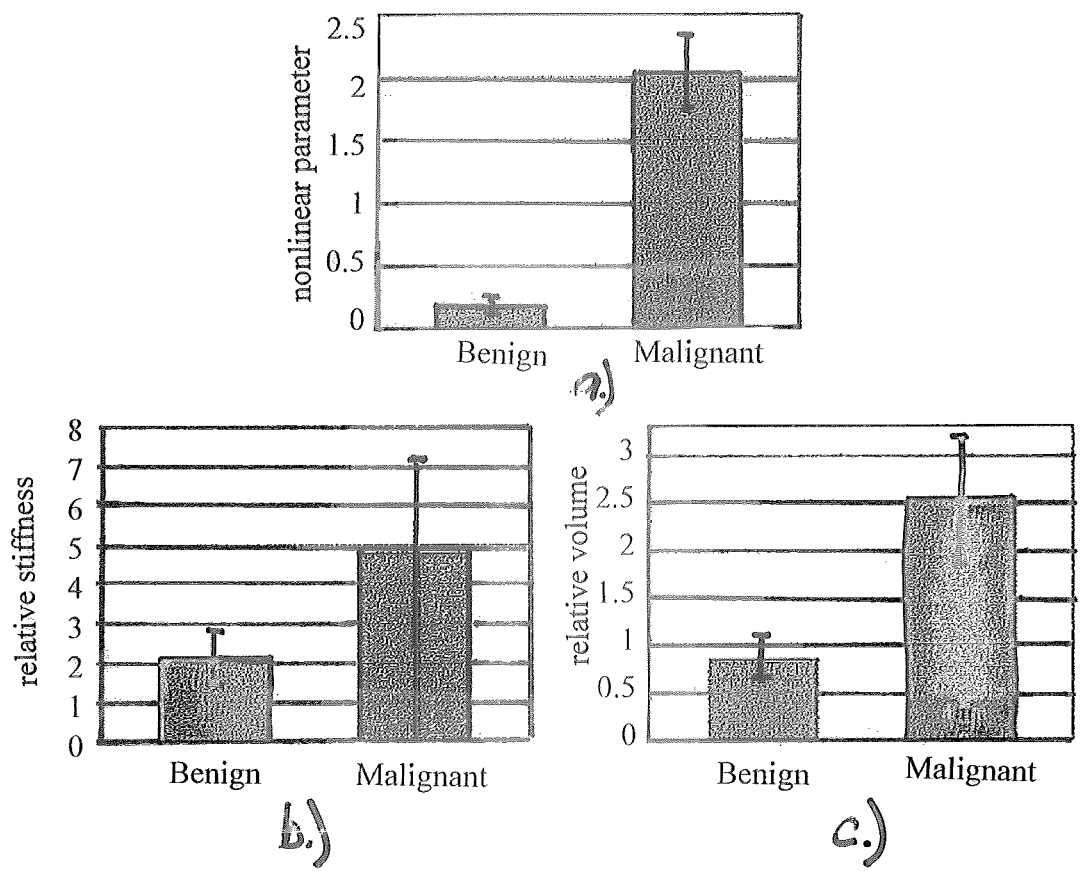
FIG. 18 Sets forth graphs 18a, 18b, and 18c that show performance comparison between the novel nonlinear parameter of the method and device of the present invention (18a), and relative stiffness (18b), and relative volume (18c) of two commonly practiced (known) parameters.
Figure 19:
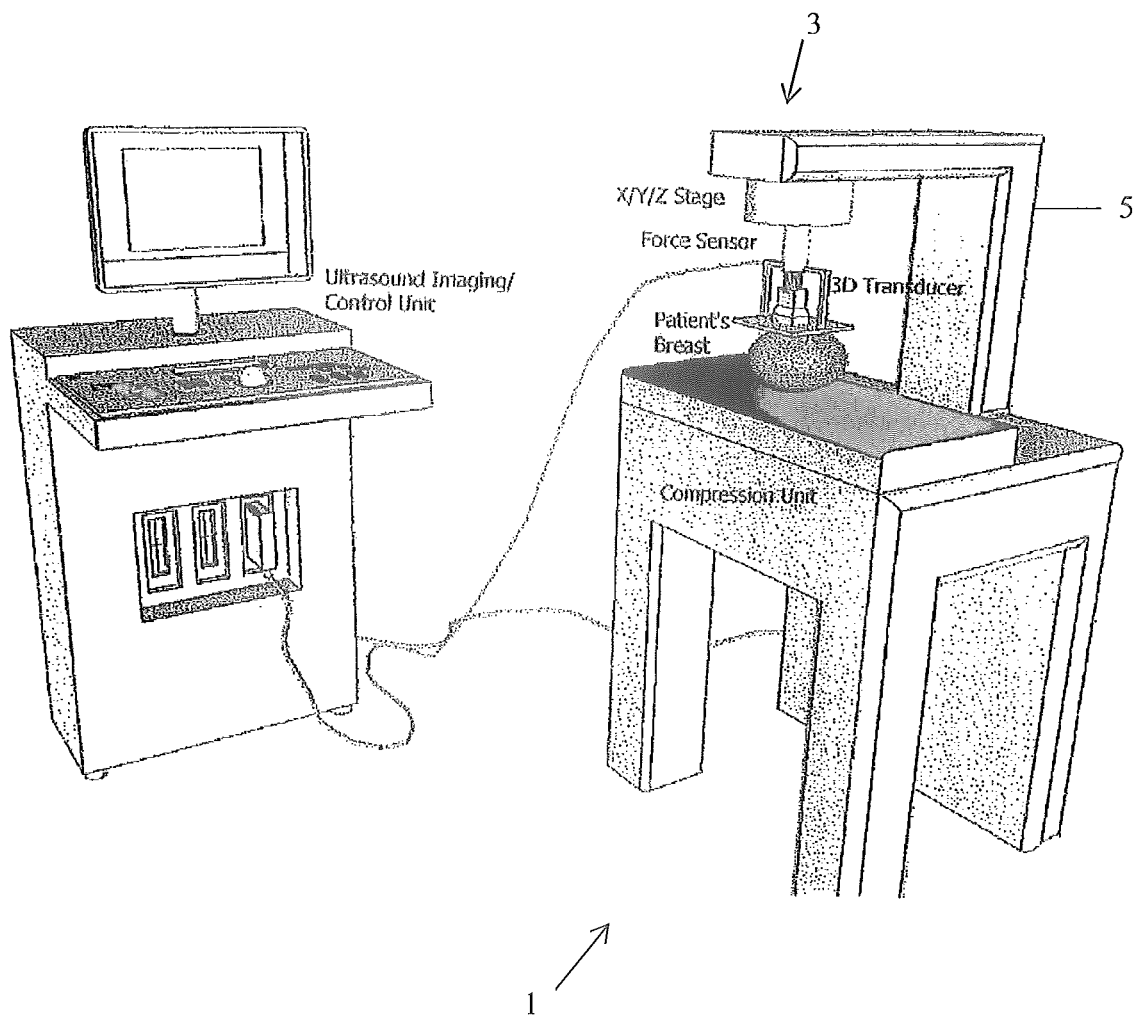
FIG. 19 Shows a preferred embodiment of a system configuration (1) of the present invention, for example but not limited to use in examining breast tissue, comprising a device (3) of the present invention having a positioning system (5), a compression unit and force sensor, and a 3D Transducer in communication with an ultrasound imaging computer processing control unit. The force sensor is in communication with the compression unit. The compression unit is preferably in communication with the ultrasound imaging computer processing control unit so that the compression levels may be increased or decreased by the operator of the ultrasound imaging computer processing control unit. The positioning system may optionally be mounted on a rotating gantry (such as for example but not limited to rotation about and around a tissue specimen from 1 to 360 degrees of freedom) so that the 3D transducer may be positioned around and about a tissue specimen to allow for flexibility in examining various body parts of the anatomy of a patient.
Figure 20:
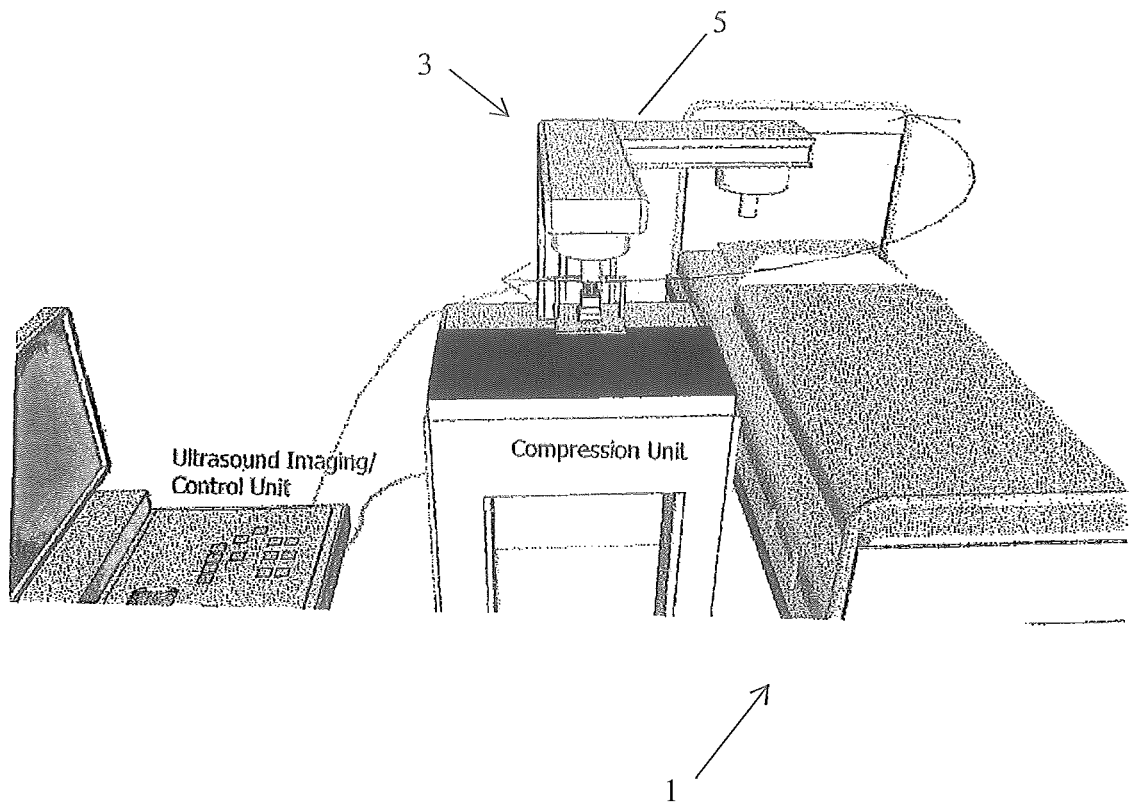
FIG. 20 Shows a preferred embodiment of a system configuration (1) of the present invention, for example but not limited to use in examining neck-liver tissue, comprising a device (3) of the present invention having a positioning system (5), a compression unit and force sensor, and a 3D Transducer in communication with an ultrasound imaging computer processing control unit. The force sensor is in communication with the compression unit. The compression unit is preferably in communication with the ultrasound imaging computer processing control unit so that the compression levels may be increased or decreased by the operator of the ultrasound imaging computer processing control unit. The positioning system (3) is optionally capable of rotating (such as for example but not limited to rotation about and around a tissue specimen from 1 to 360 degrees of freedom) so that the 3D transducer may be positioned around and about a tissue specimen to allow for flexibility in examining various body parts of the anatomy of a patient.

Equation 3 was calculated to evaluate the performance of the derived volumetric strain elastograms in vivo for both benign and malignant masses. FIG. 13 demonstrates the four elastographic volumes showing a cross sectional view of one of the benign masses. Normalization was performed for a fair comparison, as described earlier. It was observed that the boundary of the stiff mass was significantly enhanced, and the mass had a clear discrepancy from the surrounding soft tissue. This agreed well with the in vitro breast phantom results. FIG. 14 demonstrates the four elastographic volumes showing a cross sectional view of a malignant mass. Again, it was obvious from the figure that the boundary of the malignant mass was clearly seen. As shown in the breast phantom, benign and malignant cases, the maximum shear strain elastogram presents the best boundary enhancement, followed by the Von Mises strain and first principal strain, respectively. This observation showed that the derived strains can be used for both benign and malignant cases with a significant boundary enhancement over the conventionally used elastograms; i.e. normal axial strain.

Those persons skilled in the art will appreciate that the present invention provides a method comprising constructing 3D elastography volumes. This method was applied in vitro for the purpose of evaluation and parameter tuning. The method was also applied for in vivo cases. The method comprises using a mammography stage in order to apply pre-compression at three force levels, as well as to apply the small compression necessary for elastography to work. In a preferred embodiment of this invention, a modified compression paddle of the present invention as described herein, was used to hold the ultrasound probe and position it to the required region of interest. The designated maximum compression level was set to the usually used level for regular mammography imaging, so that patients would not feel extra pain. In addition, the design of the compression paddle of the present invention was operator and patient friendly. Patients did not feel uncomfortable about the imaging process, except for patients with small breasts of thicknesses less than about 5 cm, which were not included in the study. Breast thickness was measured in the vertical direction, while the breast was positioned on the mammography stage without applying any compression. Few patients had a concern about feeling numbing during compression, yet no major concerns or risks were reported during the study. Imaging session, as a whole, took about 15 minutes for each patient, which was considered to be acceptable. Most of this time was to properly position the patient on the stage and to align the ultrasound probe directly over the breast mass. The patient had to stay still and take shallow breaths only for one minute or less. This hold time was necessary to minimize motion artifacts, and it was only required during the application of the three pre-compression levels and acquisition of the RF data.

This new method of breast mass classification is based on the nonlinear mechanical behavior of stiff tumors. The use of the new nonlinear parameter, along with 3D imaging, provided an additional means of emphasizing the strain differences of the stiff mass from the surrounding soft tissue. Material nonlinearity characterization requires a large tissue deformation, which was accomplished by compressing the breast tissue from 2 to 4 Kgf. The upper limit of 4 Kgf is considered a significant deformation, where the breast tissue becomes firm, but not painful.

Calculations based on volumes are advantageous over 2D images, as they provide multiple readings per case, which would be more accurate than a single value. The estimated nonlinear parameter had an average value of 0.163±0.063 and 1.642±0.261 for benign and malignant masses, respectively. By assuming a nonlinear model and constructing an approximate force-strain curve for the stiff mass, a better distinction between mass types can be obtained using the nonlinear part of the curve. This behavior of malignant and benign masses with respect to soft tissue agrees well with the reported in vitro mechanical measurements [8, 30, 36], Emelianov et al. (see reference 31) and. Xu et al. (see reference 32) presented classification methods utilizing nonlinearity to characterize different tissue types, and their approaches involved estimating a nonlinear parameter for that purpose. Yet, their methods were based on the estimated values of axial strains for the mass only. In contrast, the method of the present invention uses the strain differences between the mass and the surrounding healthy tissue. Incorporating soft tissue strains provided a reference value at each compression level, and the behavior of the stiff mass was observed with respect to the soft tissue, rather than observing the absolute behavior of the mass by itself. As a result, malignant mass's behavior were distinct from that of the benign, because the malignant masses exhibited higher nonlinearity with respect to soft tissue.

Utilizing the strain ratio only as a classification parameter suffers from the overlap in values depicted by benign and malignant masses (see references 26-28). The current in vivo study revealed an average strain ratio value of 2.135±0.707 and 4.21±2.108 for benign and malignant masses, respectively. Multi-compression strain ratio values can also be used to estimate the nonlinear parametric classification. Yet, strain differences provided better emphasis on the nonlinearity of stiff masses and made a larger separation margin between the malignant parameter values and the benign values, as shown in FIG. 10. In addition, one of the examined patients had an invasive lobular carcinoma mass, and the strain ratio parameter failed to detect malignancy for that case. The average strain ratio was 2.06±0.12 and the value was not increasing significantly with increasing the pre-compression pressure, which indicated a benign behavior. On the other hand, the nonlinear parameter showed a value of 1.9, and that strongly suggested malignancy. This rare malignant case showed the potential of using the new nonlinear parameter in characterizing various types of breast masses.

The performance of relative mass size parameter between elastography and B-mode was good in the classification process in this study. Average values were 0.848±0.237 and 2.18±0.522 for benign and malignant masse, respectively. However, this requires the mass to be quite clear in the B-mode images, which is not the case for specific kinds of breast masses, where the mass boundary is vague. Hence many clinical studies suggested special care during performing such measurements, as it may cause erroneous decisions (see references 24, 25, and 29).

Axial shear strain did not provide useful volumetric construction, because it consists of negative and positive strain values around the stiff mass, which resulted in vague and hard to interpret volumes. Also, we did not report the second principal strain as it was very similar to the axial shear strain. Nevertheless, both strains might be useful in characterizing breast masses in 2D, as stated in previous studies (see references 38, 42, 50, and 51). Our goal here was to use the axial shear strain along with the normal strain to further enhance the boundary between soft and stiff tissues.

One limitation with the clinical study setup was using the mammography stage compression force sensor, which had low resolution readings of 0.5 Kgf. The choice of using this already available sensor was for simplifying the system design. Yet, a higher resolution force sensor would provide more accurate measurements, and more multi-compression points would be obtained, and hence make a smoother force-strain curve.

Those persons skilled in the art understand that the present invention provides a number of new strain imaging types and which are demonstrated in 3D. The results showed that the new types, especially the maximum shear strain elastogram, provide a visual improvement to breast mass imaging over the background art devices and methods. The present invention's improvement in mass's boundary preservation can be explained by the fact that the newly derived strains incorporated both material axial deformation and angular distortion from normal axial strains and axial shear strains, respectively. Both strain components play their role in the elasticity imaging process. The normal axial strain provides contrast in the direction of the mechanical compression, while the axial shear strain provides contrast with a slip angle from axial direction of the mechanical compression. Shear slip mechanism at the interface between two dissimilar materials is the main factor for the potential boundary enhancement.

In FIGS. 13 and 14, the observed degree of boundary enhancement in the plots was different. This can be explained by the relative location of the mass with respect to the sector probe in each case examined, which was slightly different and caused a different shear stress distribution over the masses. The compression pressure profile of the sector probe also has a sector shape, which leads to low pressure on the edges of the scanned areas, with the pressure gradually increasing towards the middle. This results in higher induced strain directly under the probe and decreasing as we move to the edges. This effect occurs also in the elevational direction, because of the circular foot print of the probe. To reduce this effect, a 3D linear probe is recommended. Yet, the resultant volumes showed the clear mass boundary enhancement in the examined cases.

Automatic segmentation techniques based on active contour methods (see reference 52) can be optimized using maximum shear elastography. Those types of segmentation algorithms have the limitation of requiring the masses to be relatively regular, and well-circumscribed, with single margins on the images, which is not the case with breast masses. This limitation can be overcome by using the newly derived elastography strains, as the boundaries become more profound in the resulting images and volumes.

In summary, the present invention provides a method and device that provides in vivo 3D elastography. The device and method of the present invention includes the ability to better diagnose stiff masses inside soft tissues. Those persons skilled in the art appreciate that the present invention provides a new breast mass classification method based on a power law behavior of the strain values of the soft and stiff tissues at different pre-compression levels. The method was tested on human subjects in vivo and outcomes were verified with the biopsy results described herein. The results show that the use of the new nonlinear parameter can help increase the overall efficiency of elastography in classifying breast masses, hence limiting the number of unnecessary biopsy procedures. Using strain ratio for classification suffered from a large overlap in values between benign and malignant cases. Relative mass size proved to be a good classification parameter. Yet the mass needs to be well bounded and very clear in the B-mode images to get an accurate diagnosis, which is not always the case for breast masses.

In addition, new elastography volumetric strain types were described herein, and their usage in emphasizing the stiff mass's boundary was demonstrated.

REFERENCES

1. World cancer report, International Agency for Research on Cancer (IARC), 2008.
2. American cancer society. Breast cancer facts & FIGS. 2011-2012, Atlanta: American Cancer Society, Inc., 2011.
3. N. Houssami, S J. Lord, S. Ciatto, Breast cancer screening: Emerging role of new imaging techniques as adjuncts to mammography, Medical Journal of Australia, 190 (2009) 493-498.
4. R A. Carney, D. L. Miglioretti, B. C. Yankaskas, K. Kerlikowske, R. Rosenberg, C. M. Rutter, B. M. Geller, L. A. Abraham, S. H. Taplin, M. Dignan, G. Cutter, R. Ballard-Barbash, Individual and combined effects of age, breast density, and hormone replacement therapy use on the accuracy of screening mammography, Ann Intern Med, 138 (2003) 168-175.
5. S. P. Poplack, P. A. Carney, J. E. Weiss, L. Titus-Emstoff, M. E. Goodrich, A. N A. Tosteson, Screening mammography: Costs and use of screening-related services, Radiology, 234 (2005) 79-85.
6. E. S. Burnside, T J. Hall, A. M. Sommer, G. K. Hesley, G A. Sisney, W. E. Svensson, J. P. Fine, J. J. Jiang, N. J. Hangiandreou, Differentiating benign from malignant solid breast masses with us strain imaging. Radiology, 245 (2007) 401-410.
7. G. Scaperrotta, C. Ferranti, C. Costa, L. Mariani, M. Marchesini, L. Suman, C. Folini, S. Bergonzi, Role of sonoelastography in non-palpable breast lesions, European Radiology, 18 (2008) 2381-2389.
8. T. A. Krouskop, T. M. Wheeler, F. Kallel, B. S. Gana, T. Hall, Elastic moduli of breast and prostate tissues under compression, Ultrasonic Imaging, 20 (1998) 260-274.
9. A. L. Zhang, L. X. Xu, G A. Sandison, J. Y. Zhang, A microscale model for prediction of breast cancer cell damage during cryosurgery, Cryobiology, 47 (2003) 143-154.
10. M. M. Doyley, J. C. Bamber, F. Fuechsel, N. L. Bush, A freehand elastographic imaging approach for clinical breast imaging: System development and performance evaluation, Ultrasound Med Biol, 27 (2001) 1347-1357.
11. R J. Housden, A. H. Gee, G. M. Treece, R. W. Prager, 3-d ultrasonic strain imaging using freehand scanning and a mechanically-swept probe, IEEE Transactions on Ultrasonics Ferroelectrics and Frequency Control, 57 (2010) 501-506.
12. M. A. Lubinski, S. Y. Emelianov, M. O'Donnell, Adaptive strain estimation using retrospective processing, IEEE Transactions on Ultrasonics Ferroelectrics and Frequency Control, 46 (1999) 97-107.

13. J. Ophir, 1. Cespedes, H. Ponnekanti, Y. Yazdi, X. Li, Elastography—a quantitative method for imaging the elasticity of biological tissues, Ultrasonic Imaging, 13 (1991) 111-134.
14. L Cespedes, J. Ophir, Reduction of image noise in elastography, Ultrasonic Imaging, 15 (1993) 89-102.
15. A. V. Patil, C. D. Garson, J. A. Hossack, 3d prostate elastography: Algorithm, simulations and experiments, Phys Med Biol, 52 (2007) 3643-3663.
16. R. Zahiri-Azar, S. E. Salcudean, Motion estimation in ultrasound images using time domain cross correlation with prior estimates, IEEE Transactions on Biomedical Engineering, 53 (2006) 1990-2000.
17. R. Zahiri-Azar, S. E. Salcudean, Time-delay estimation in ultrasound echo signals using individual sample tracking, IEEE Transactions on Ultrasonics Ferroelectrics and Frequency Control, 55 (2008) 2640-2650.
18. H. Chen, T. Varghese, Multilevel hybrid 2d strain imaging algorithm for ultrasound sector/phased arrays, Med Phys, 36 (2009) 2098-2106.
19. K. Liu, P. F. Zhang, J. H. Shao, X. J. Zhu, Y. Zhang, J. Bai, A 2d strain estimator with numerical optimization method for soft-tissue elastography, Ultrasonics, 49 (2009) 723-732.
20. S. K. Alam, J. Ophir, E. E. Konofagou, An adaptive strain estimator for elastography, IEEE Transactions on Ultrasonics Ferroelectrics and Frequency Control, 45 (1998) 461-472.
21. S. Bharat, T. G. Fisher, T. Varghese, T. J. Hall, J. Jiang, E. L. Madsen, J. A. Zagzebski, F T. Lee, Three-dimensional electrode displacement elastography using the siemens c7f2 foursight four-dimensional ultrasound transducer, Ultrasound Med Biol, 34 (2008) 1307-1316
22. J. F. Deprez, E. Brusseau, C. Schmitt, G. Cloutier, O. Basset, 3d estimation of soft biological tissue deformation from radio-frequency ultrasound volume acquisitions, Medical Image Analysis, 13 (2009) 116-127.
23. G. M. Treece, I. E. Lindop, A. H. Gee, R. W. Prager, Freehand ultrasound elastography with a 3-d probe. Ultrasound Med Biol, 34 (2008) 463-474.
24. B. S. Garra, E. L Cespedes, J. Ophir, S. R. Spratt, R. A. Zuurbier, C. M. Magnant, M. F. Pennanen, Elastography of breast lesions: Initial clinical results, Radiology, 202 (1997) 79-86.
25. T J. Hall, Y. N. Zhu, C. S. Spalding, In vivo real-time freehand palpation imaging, Ultrasound Med Biol, 29 (2003) 427-435.
26. D. Kotsianos-Hermle, K. M. Hiltawsky, S. Wirth, T. Fischer, K. Friese, M. Reiser, Analysis of 107 breast lesions with automated 3d ultrasound and comparison with mammography and manual ultrasound, Eur J Radiol, 71 (2009) 109-115.
27. H. Zhi, X. Y. Xiao, H. Y. Yang, B. Ou, Y. L. Wen, B. M. Luo, Ultrasonic elastography in breast cancer diagnosis: Strain ratio vs 5-point scale, Acad Radiol, 17 (2010) 1227-1233.
28. F. K. W. Schaefer, I. Heer, P. J. Schaefer, C. Mundhenke, S. Osterholz, B. M. Order, N. Hofheinz, J. Hedderich, M. Heller, W. Jonat, I. Schreer, Breast ultrasound elastography-results of 193 breast lesions in a prospective study with histopathologic correlation, Eur J Radiol, 77 (2011) 450-456.
29. R. G. Barr, Sonographic breast elastography, J Ultras Med, 31 (2012) 773-783.
30. Parris Wellman, Robert Howe, Edward Dalton, K. A. Kern, Breast tissue stiffness in compression is correlated to histological diagnosis, Technical Report, Harvard Biorobotics Laboratory, 1999, pp. 1-15.
31. S. Y. Emelianov, R. Q. Erkamp, M. A. Lubinski, A. R. Skovoroda, M. O'Donnell, Nonlinear tissue elasticity: Adaptive elasticity imaging for large deformations, Ultrason, (1998) 1753-1756.
32. J. R Xu, S. Tripathy, J. M. Rubin, R. W. Stidham, L A. Johnson, R D. R. Higgins, K. Kim, A new nonlinear parameter in the developed strain-to-applied strain of the soft tissues and its application in ultrasound elasticity imaging, Ultrasound Med Biol, 38 (2012) 511-523.
33. Y. R Qiu, M. Sridhar, J. K. Tsou, K. K. Lindfors, M. R Insana, Ultrasonic viscoelasticity imaging of nonpalpable breast tumors: Preliminary results, Acad Radiol, 15 (2008) 1526-1533.
34. M. Sridhar, M. F. Insana, Ultrasonic measurements of breast viscoelasticity, Med Phys, 34 (2007) 4757-4767.
35. A A. Oberai, N. H. Gokhale, S. Goenezen, R E. Barbone, T. J. Hall, A. M. Sommer, J. R Jiang, Linear and nonlinear elasticity imaging of soft tissue in vivo: Demonstration of feasibility, Phys Med Biol, 54 (2009) 1191-1207.
36. Jonathan Ophir, S. Kaisar Alam, Brian S. Garra, Faouzi Kallel, Elisa E. Konofagou, Thomas Krouskop, Christopher R. B. Merritt, Raffaella Righettr, Remi Souchon, Seshadri Srinivasan, T Varghese, Elastography: Imaging the elastic properties of soft tissues with ultrasound, J Med Ultrasonics, 29 (2002) 155-171.
37. E. E. Konofagou, T. Harrigan, J. Ophir, Shear strain estimation and lesion mobility assessment in elastography, Ultrasonics, 38 (2000) 400-404.
38. A. Thitaikumar, R. Righetti, T. A. Krouskop, J. Ophir, Resolution of axial shear strain elastography, Phys Med Biol, 51 (2006) 5245-5257.
39. A. Thitaikumar, L. M. Mobbs, C. M. Kraemer-Chant, B. S. Garra, J. Ophir, Breast tumor classification using axial shear strain elastography: A feasibility study, Phys Med Biol, 53 (2008) 4809-4823.
40. J. Ophir, S. Srinivasan, R. Righetti, A. Thittai, Elastography: A decade of progress (2000-2010), Curr Med Imaging Rev, 7 (2011) 292-312.
41. H. Y. Xu, M. Rao, T. Varghese, A. Sommer, S. Baker, T. J. Hall, G. A. Sisney, E. S. Bumside, Axial-shear strain imaging for differentiating benign and malignant breast masses. Ultrasound Med Biol, 36 (2010) 1813-1824.
42. A. K. Thittai, J. M. Yamal, L. M. Mobbs, C. M. Kraemer-Chant, S. Chekuri, B. S. Garra, J. Ophir, Axial-shear strain elastography for breast lesion classification: Further results from in vivo data. Ultrasound Med Biol, 37 (2011) 189-197.
43. E. Konofagou, J. Ophir, A new elastographic method for estimation and imaging of lateral displacements, lateral strains, corrected axial strains and poisson's ratios in tissues, Ultrasound Med Biol, 24 (1998) 1183-1199.
44. R. G. R Lopata, M. M. Nillesen, H. H. G. Hansen, L H. Gerrits, J. M. Thijssen, C. L. de Korte, Performance evaluation of methods for two-dimensional displacement and strain estimation using ultrasound radio frequency data, Ultrasound Med Biol, 35 (2009) 796-812.
45. S. J. Orfanidis, Optimum signal processing an introduction, Second Edition ed., Sophocles J. Orfanidis, 2007.
46. R. Righetti, J. Ophir, P. Ktonas, Axial resolution in elastography, Ultrasound Med Biol, 28 (2002) 101-113.
47. H. Y Xu, T. Varghese, E. L. Madsen, Analysis of shear strain imaging for classifying breast masses: Finite element and phantom results, Med Phys, 38 (2011) 6119-6127.

48. A. Thitaikumar, T. A. Krouskop, J. Ophir, Signal-to-noise ratio, contrast-to-noise ratio and their trade-offs with resolution in axial-shear strain elastography, Phys Med Biol, 52 (2007) 1328.
49. Serope Kalpakjian, S. Schmid, Manufacturing processes for engineering materials, 5 ed., Prentice Hall, 2007
50. A. Thitaikumar, T A. Krouskop, B. S. Gana, J. Ophir, Visualization of bonding at an inclusion boundary using axial-shear strain elastography: A feasibility study, Phys Med Biol, 52 (2007) 2615-2633.
51. L. J. Chen, R J. Housden, G. M. Treece, A. H. Gee, R. W. Prager, A normalization method for axial-shear strain elastography, IEEE Transactions on Ultrasonics Ferroelectrics and Frequency Control, 57 (2010) 2833-2838.
52. W. Liu, J A. Zagzebski, T. Varghese, C. R. Dyer, U. Techavipoo, T. J. Hall, Segmentation of elastographic images using a coarse-to-fine active contour model, Ultrasound Med Biol, 32 (2006) 397-408.

We claim:

1. A method for classifying and characterizing a tumor of a patient as either benign or malignant comprising:
    positioning a tissue or organ of a patient on a compression stage;
    aligning a 3D (three dimensional) ultrasound probe on or close in position to the tissue or organ suspected of having a tumor, said probe capable of performing 3D ultrasound strain imaging elastography, and wherein said probe having a force sensor for obtaining force measurement;
    performing 3D ultrasound strain imaging elastography to said tissue or organ and obtaining a pre-compression raw 3D volumetric data of said tissue or organ;
    applying a first compression force to the tissue or organ having the suspected tumor for forming a first compressed tissue or organ;
    performing 3D ultrasound strain imaging elastography to said first compressed tissue or organ for obtaining a first compressed tissue raw 3D volumetric data for estimating a first tissue strain of said first compressed tissue or organ;
    applying a second compression force to the first compressed tissue or organ, wherein the second compression force is greater than the first compressive force for forming a second compressed tissue or organ;
    performing 3D ultrasound strain imaging elastography to said second compressed tissue or organ for obtaining a second compressed tissue raw 3D volumetric data for estimating a second tissue strain of said second compressed tissue or organ;
    applying a third compression force to the second compressed tissue or organ, wherein the third compression force is greater than the second compression force for forming a third compressed tissue or organ;
    performing 3D ultrasound strain imaging elastography to said third compressed tissue or organ for obtaining a third compressed tissue raw 3D volumetric data for estimating a third tissue strain of said third compressed tissue or organ;
    providing a nonlinear parameter computer processing unit in communication with a 3D ultrasound transducer, and transferring said pre-compression raw 3D volumetric data, said first compressed tissue raw 3D data, said second compressed tissue raw 3D data, and said third compressed tissue raw 3D data from the 3D ultrasound transducer to said nonlinear parameter computer processing unit, wherein said nonlinear parameter computer processing unit constructs strain images and 3D volumes for each of said precompression, and said first, second, and third compressed tissue or organ, wherein said 3D volumes include axial strain, first principal, maximum shear, and VonMises strains incorporating normal axial strain and axial shear strain together for distinguishing a stiff mass of a suspect tumor from a background soft tissue surrounding said stiff mass, and performs a tissue characterization and classification procedure using an estimated nonlinear biomechanical tissue parameter model described by a nonlinear elastic power law behavior as $f=A(\Delta\epsilon)^n$ where f is an applied force level, $\Delta\epsilon$ is a strain difference between said suspect tumor and said background soft tissue, and A and n are fitting parameters, including constructing strain elastography volumes at each of said compression levels, calculating a strain difference value between said suspect tumor and said background soft tissue at each of said compression levels in an absence of comparing hue values of a band of pixels inside and outside of a contour of said suspect tumor, calculating a rate of change of strain difference values resulting in a strain ratio value in the absence of comparing hue values of a band of pixels inside and outside of said contour of said suspect tumor, and determining whether the tissue or organ has a benign tumor or a malignant tumor.

2. The method of claim 1 including wherein the first, second and third compression force is pressure applied against the tissue or organ.

3. The method of claim 1, wherein said first compression force, said second compression force, and said third compression force comprise separate compression levels, and classifying the suspect tumor as benign if the strain ratio value ranges from greater than zero to 2.85 indicating a weak nonlinear behavior for the suspect tumor, or classifying the suspected tumor as malignant if the strain ratio value ranges from 4.21 to greater than 6.3 indicating a high nonlinear behavior.

4. A device comprising a 3D ultrasound transducer configured to acquire raw image and 3D volumetric data when positioned against and scanning a tissue or organ of a patient, a nonlinear parameter computer processing unit in communication with said 3D ultrasound transducer for analyzing the raw data transferred from the 3D ultrasound transducer to said nonlinear parameter computer processing unit, said nonlinear parameter computer processing unit configured to perform a function of constructing a final set of strain images and 3D volumes from a pre-compressed tissue or organ, and multiple compression of tissue or organ and ultrasound raw data wherein said strain images and the 3D volumes for each of said precompressed and multiple compressed tissues or organs include axial strain, first principal, maximum shear, and VonMises strains incorporating a normal axial strain and an axial shear strain together for distinguishing a stiff mass of a suspect tumor from a background soft tissue, and performs a classification of the tissue or organ using a nonlinear biomechanical analysis of said acquired 3D volumetric raw data for constructing strain elastography volumes at each of said multiple compressed tissues or organs, calculating a strain difference value between said suspect tumor and said background soft tissue at each of said compressions described by a nonlinear elastic power law behavior as $f=A(\Delta\epsilon)^n$ where f is an applied force level, $\Delta\epsilon$ is a strain difference between said suspect tumor and said background soft tissue, and A and n are fitting parameters, in an absence of comparing hue values of a band of pixels inside and outside of a contour of said suspect tumor, calculating the rate of change of strain difference values resulting in a strain ratio value in the absence of comparing hue values of a band of pixels inside and outside of said contour of said suspect tumor, and a compression stage for applying pressure against the tissue or organ of a patient, wherein said compression stage is in communication with said nonlinear parameter computer processing unit.

5. The device of claim 4 including wherein said compression stage applies continuous force measurements to the tissue or organ, and a force gauge that is attached to and that is in communication with said 3D ultrasound transducer for providing continuous force measurements providing a smooth force-strain measurement.

6. The device of claim 4 wherein said 3D ultrasound transducer uses an ultrasound linear array.

7. The device of claim 4 wherein the 3D ultrasound transducer is a linear probe that is either a mechanically swept 1-D array, or a 2-D array of transducers.

8. The device of claim 4 wherein said compression stage is a motorized standalone compression stage for obtaining force measurements, said motorized compression stage having maneuvering flexibility around the suspect tissue or organ, and a compression stage computer processor for performing a function of controlling said motorized compression stage.

9. The device of claim 4 including a vertical and horizontal movement positioning system wherein said 3D ultrasound transducer is in communication with said vertical and horizontal positioning system, and wherein said vertical and horizontal positioning system performs a function of moving said 3D ultrasound transducer or moving said tissue or organ of a patient.

10. The device of claim 8 including wherein said motorized compression stage holds said 3D ultrasound transducer for maneuvering said 3D ultrasound transducer.

11. The device of claim 8 wherein said motorized compression stage has an aperture for allowing the 3D ultrasound transducer to scan a localized area of interest of a tissue or organ.

12. The device of claim 9 wherein said motorized compression stage applies said multiple compressions to the tissue or organ.

13. The device of claim 4 wherein said 3D ultrasound transducer comprises either mechanically actuated array of piezoelectric elements, or a two dimensional array of elements, wherein said 3D transducer acquires raw radiofrequency (RF) signals when applied against the tissue or organ of a patient.

14. The device of claim 4 including wherein said compression stage is one or more compression paddles.

15. The device of claim 14 including wherein said paddle has an aperture to accommodate a probe of the 3D ultrasonic transducer.

16. The device of claim 14 including wherein said compression paddle is deformable under pressure.

17. The method of claim 1 further comprising at least one additional sequence of applying a successive compression force to the compressed tissue or organ in addition to said first, second, and third compressive forces, wherein the successive compression force is greater than a prior compression force for forming a successive compressed tissue or organ; and performing 3D ultrasound strain imaging elastography to said successive compressed tissue or organ for obtaining at least one additional compressed tissue raw 3D volumetric data for estimating a successive tissue strain.

* * * * *